United States Patent [19]

Schweiger

[11] 4,419,316

[45] Dec. 6, 1983

[54] PROCESS OF MAKING FILMS, FIBERS OR OTHER SHAPED ARTICLES CONSISTING OF, OR CONTAINING, POLYHYDROXY POLYMERS

[76] Inventor: Richard G. Schweiger, San Jose, Calif.

[21] Appl. No.: 201,806

[22] Filed: Oct. 29, 1980

Related U.S. Application Data

[60] Continuation of Ser. No. 945,252, Sep. 25, 1978, abandoned, which is a continuation of Ser. No. 794,145, May 5, 1977, abandoned, which is a division of Ser. No. 669,483, Mar. 23, 1976, Pat. No. 4,035,569, which is a continuation of Ser. No. 487,196, Jul. 10, 1974, abandoned, which is a continuation-in-part of Ser. No. 298,580, Oct. 18, 1972, abandoned, which is a continuation-in-part of Ser. No. 40,442, May 25, 1970, Pat. No. 3,702,943.

[51] Int. Cl.$^3$ ............... D01F 11/02; D01F 11/04; C08L 1/16; C08L 5/00

[52] U.S. Cl. ............... 264/184; 106/128; 106/168; 106/169; 106/195; 106/203; 106/205; 106/208; 106/213; 252/8.5 A; 264/185; 264/186; 264/187; 264/218; 424/343; 426/105; 427/339; 427/385; 428/439; 524/27; 524/35; 524/51; 524/55; 525/57

[58] Field of Search ............... 525/57; 524/27, 35, 524/51, 55; 264/184-187, 210; 106/168, 169, 205, 208, 210, 213

[56] References Cited

U.S. PATENT DOCUMENTS

| | | | |
|---|---|---|---|
| 2,239,718 | 4/1941 | Izard | 525/57 |
| 2,676,929 | 4/1954 | Duddy | 260/17.4 ST |
| 2,895,786 | 7/1959 | Schlack | 525/57 |
| 3,133,890 | 5/1964 | Britton | 525/57 |
| 3,200,091 | 8/1965 | Seperlund et al. | 260/17.4 ST |
| 3,215,137 | 11/1965 | Laakso | 260/17.4 ST |
| 3,236,669 | 2/1966 | Williams | 8/116 R |
| 3,312,641 | 4/1967 | Young | 260/17.4 ST |

FOREIGN PATENT DOCUMENTS

| | | |
|---|---|---|
| 786225 | 5/1968 | Canada. |
| 876148 | 7/1971 | Canada. |
| 899559 | 5/1972 | Canada. |

OTHER PUBLICATIONS

J.A.C.S., 69, pp. 1636-1640 (1947).
156th ACS Nat. Meeting, Div. of Cellulose, Wood and Fiber Chem., Abstracts, No. 15 (1968).
CA, 68, 41234b (1968).
Chem. and Ind. p. 296 (3-1969).

*Primary Examiner*—Stanford M. Levin
*Attorney, Agent, or Firm*—Beehler, Pavitt, Siegemund, Jagger & Martella

[57] ABSTRACT

A process of preparing film, fibers and other shaped articles by nitrosating a polyhydroxy polymer in a reaction medium containing a solubilizing agent for the resulting polyhydroxy polymer nitrite ester and a suitable proton acceptor, bringing the reaction mixture into the desired shape and regenerating and separating the polyhydroxy polymer by contact with a protic solvent in the presence of an acid catalyst. The polyhydroxy polymer may be a polyvinyl alcohol, cellulose or other polysaccharide, and mixtures thereof. Also dissolved in the reaction medium may be an organic solvent soluble polymer substantially lacking hydroxyl groups. If mixtures of polyhydroxy polymers or of polyhydroxy polymers lacking hydroxyl groups and organic solvent soluble polymers are employed the resulting films, fibers or other shaped articles consist of homogeneous and intimate mixtures of all the polymers originally present in solution. Solutions containing polyhydroxy polymer nitrite ester or a mixture of polyhydroxy polymer nitrite ester and organic solvent soluble polymer lacking hydroxyl groups in an anhydrous medium containing a highly polar aprotic solvent or a weak tertiary amine base or both are disclosed.

54 Claims, No Drawings

PROCESS OF MAKING FILMS, FIBERS OR OTHER SHAPED ARTICLES CONSISTING OF, OR CONTAINING, POLYHYDROXY POLYMERS

This application is a continuation of application Ser. No. 945,252, abandoned, filed Sept. 25, 1978, which in turn is a continuation of application Ser. No. 794,145, abandoned, filed May 5, 1977, which in turn is a division of application Ser. No. 669,483, U.S. Pat. No. 4,035,569, filed Mar. 23, 1976, which in turn is a continuation of application Ser. No. 487,196, abandoned, filed July 10, 1974, which in turn is a continuation-in-part of application Ser. No. 298,580, abandoned, filed Oct. 18, 1972, which in turn is a continuation-in-part of application Ser. No. 040,442 filed May 25, 1970, and now U.S. Pat. No. 3,702,943.

Ester derivatives of polyhydroxy polymers are known and have been described extensively in the prior art literature. The chemical and physical properties of such ester derivatives depend to a large extent on the particular nature of the polymer, its molecular weight, the type of ester substituent group, and the degree of substitution of the polymer (hereinafter referred to as D.S.). Due to the manner in which ester derivatives of polyhydroxy polymers have previously been prepared, the D.S. of the resulting ester derivatives has not been relatively uniform. This has produced ester derivatives whose properties, e.g., water solubility and compatibility with various metallic ions, have not been generally satisfactory and has restricted the use areas for the ester derivatives.

In accord with the present invention, it has been found the esterified polyhydroxy polymers having novel and unusual properties may be prepared from nitrite esters of the polyhydroxy polymers. The nitrite esters are employed in the present invention as reaction intermediates because of the instability of the nitrite ester groups and the solubility of the ester in the reaction medium. Through use of the nitrite ester intermediates, polymeric products, such as nitrate esters or sulfate esters of polyhydroxy polymers, are obtained which have novel properties and a generally uniform substitution of nitrate or sulfate ester groups among the polymer units. Due to the relative instability of the nitrite ester groups, polyhydroxy polymer nitrites may be used also for making films, fibers and other shaped articles consisting of homogeneous mixtures of various polyhydroxy polymers or of one or more polyhydroxy polymers and one or more other polymers.

In the formation of an ester derivative of a polyhydroxy polymer according to the present invention, the amount of depolymerization resulting from the reaction is negligible. Thus, products are obtained which have very high solution viscosities. In the case of sulfate esters of polyhydroxy polymers, I have obtained, for example, products whose solution viscosities are many times greater than the solution viscosities of superficially similar sulfate esters produced by prior art methods.

In addition, it is possible according to the invention to produce esterified polyhydroxy polymers which have D.S. values that cannot be obtained by previously known methods. As an example, I have prepared cellulose sulfate esters having a low D.S., e.g., less than about 0.3 in which the ester groups are substantially uniformly distributed among the cellulose polymer units. Also, I have obtained sulfuric acid esters of locust beam gum and guar gum which have a D.S. of above 1. Still further, I have prepared water soluble nitrate esters of polyhydroxy polymers having a D.S. of less than 1. The properties of these nitrate esters are especially surprising since previous nitrate esters of polyhydroxy polymers have, in general, been highly substituted and insoluble in water.

The relatively uniform distribution of the ester substituent groups over the macromolecule obtainable according to the invention results, in part, from the fact that the polymeric nitrite intermediate used in the reaction is solvated or even dissolved in the reaction medium. In contrast, in prior art methods, the polymeric starting material was generally suspended in the reaction medium in the form of insoluble particles. The homogeneity of the products prepared according to the present invention is of particular importance when the D.S. of the esterified products is considerably below the maximum D.S. for the particular polyhydroxy polymer, such as in the sulfate esters of the invention and particularly in the case of the cellulose sulfate esters. For example, in previous sulfation procedures, e.g., in preparation of cellulose sulfate esters, insoluble cellulose fiber was used as the starting material. In sulfating the fiber, the reaction mechanism involved the so-called "Peeling Process", in which the fiber surface was first partially substituted, then solvated and removed by the reaction medium, and then highly substituted by reaction with excess sulfation reagent in the reaction medium. During the "Peeling Process", the next inner layer of the cellulose fiber was then exposed and sulfated in a similar fashion with the process proceeding until most of the fiber or the sulfation reagent was consumed.

As a result of the "Peeling Process," the polymeric sulfates which were previously obtained were highly substituted and had a D.S. relatively close to the maximum for the polymer irrespective of the amount of sulfation reagent employed. Even when the average D.S. of the polymer was less than the maximum D.S. of the polymer, the distribution of ester substituent groups was not uniform and a considerable number of the polymer units were fully substituted while other polymer units had a very low D.S. or were not substituted at all. These drawbacks are prevented by the present invention since the nitrite ester used as an intermediate is solvated or solubilized and the ester substituent groups in the final products are, thus, distributed substantially uniformly among the polymer units of the product. Thus, in cellulose sulfate products of the invention having a D.S. of 2 or 1, substantially all of the polymer units in the cellulose will contain only two sulfate ester groups or one sulfate ester group.

Due to the substantially uniform distribution of ester groups among the polymer units in the products of the present invention, the products have, in general, unusual solubility characteristics. Also, solutions of the products have unusual compatibilities with metallic ions. For example, cellulose sulfate products provided according to the invention which have a D.S. of about 0.3 to about 1 are soluble in water. This is quite surprising since the prior literature reports that colloidal cellulose sulfate must have a D.S. in excess of 1 in order to be water soluble.

In addition, sulfate esters of polyhydroxy polymers of the present invention are also markedly different from superficially similar materials of the prior art in terms of their compatibiities with a wide variety of metallic ions and also their compatibilities with relatively high concentrations of metallic ions. Still further differences are observed between the products of the present invention and superficially similar materials of the prior art, e.g., sulfates of polyhydroxy polymers, in terms of reactivity with water soluble proteins.

As disclosed in my prior application Ser. No. 298,580, one aspect of the present invention is directed to a process for the preparation of nitrate esters or sulfate esters of a polyhydroxy polymer which is a polysaccharide or a polyvinyl alcohol that is partially substituted with ether or ester groups. Etherified and esterified polysaccharides or polyvinyl alcohol are known materials which may include, for example, substituent groups such as formate, acetate, carboxymethyl, methyl ether, ethyl ether, and propionate groups. Typical of the known etherified and esterified materials which may be employed as starting materials are carboxymethyl cellulose, methyl cellulose, hydroxyethyl cellulose, alginic acid acetate, alginic acid propionate; starch phosphate, hydroxylpropyl guar, pectic acid butyrate, carboxymethyl starch, partially hydrolyzed polyvinyl acetate, natural sulfate esters such as carrageenan, natural acetyl esters such as gum karaya and xanthan gum, etc.

In the formation of nitrate or sulfate esters of etherified or esterified polysaccharides or polyvinyl alcohol, according to the present invention, it is necessary that the reactant materials contain free hydroxy groups. Thus, the etherified or esterified polysaccharide or polyvinyl alcohol used as the starting material is only partially substituted and contains free hydroxyl groups which are utilized as reactant sites in accord with the invention. The free hydroxyl groups on the etherified or esterified starting materials may, thus, be nitrosated, nitrated and also sulfated in a manner similar to the nitrosation, nitration, and sulfation of the unsubstituted polyhydroxy polymers to provide the corresponding ester derivatives of the partially etherified or esterified polyhydroxy polymers.

The nitrite esters of polyhydroxy polymers, employed as reaction intermediates in the present invention, are prepared by nitrosating a suspension of the desired polyhydroxy polymer starting material in a suitable organic solvent at a reaction temperature of below about 50° C. The nitrosating reactant is preferably dinitrogentetroxide which is in equilibrium with its monomer nitrogen dioxide. Through use of the nitrite ester as a reaction intermediate, nitrate and sulfate esters of polysaccharides and polyvinyl alcohol can be readily synthesized in accord with the present invention. The resulting nitrate and sulfate ester products show a negligible degree of depolymerization and a selective degree of esterification. Also, the nitrate and sulfate ester products are distinguished by their homogeneity of substitution, i.e., the ester groups, such as sulfate ester groups, are relatively homogeneously distributed over the macromolecule. Thus, the properties of the products differ substantially from the properties of superficially similar products of the prior art in providing higher viscosities and in being compatible with certain metallic ions.

Water soluble nitrate esters may be easily prepared from the corresponding nitrite esters in accord with the invention by simply heating the solvated nitrite esters in the presence of nitric acid and removal of residual nitrite groups by treatment with a protic solvent. The resulting nitrate ester product is soluble in water, is relatively undegraded, and its aqueous solutions also tolerate relatively large amounts of water miscible organic solvents.

Polymeric sulfate esters are also prepared in accord with the present invention by sulfating the nitrite ester of a polysaccharide or polyvinyl alcohol with sulfur trioxide or a complex thereof at a relatively low reaction temperature. Thereafter, residual nitrite ester groups are removed from the polymer by reaction with a protic solvent to provide a relatively undegraded polymeric sulfuric acid ester. The sulfuric acid ester may then be neutralized or made slightly alkaline to provide the more stable salt form of the ester. The undegraded alkali ester salts are highly soluble and their aqueous solutions possess a high viscosity. Thus, the sulfate ester salts are useful as thickeners in aqueous media.

Typical of known polyhydroxy polymers which may be utilized as starting materials are the polysaccharides such as cellulose, starch, hemicellulose, guar gum, locust bean gum, gum arabic and the mannans; the polyuronic acids typified by alginic and pectic acids, and the synthetic polyhydroxy polymers such as polyvinyl alcohol. In accord with one aspect of the invention, the partially etherified or esterified polyhydroxy polymers, as described previously, are used as starting materials in the preparation of nitrate esters or sulfate esters of the partially substituted polyhydroxy polymers.

The starting polyhydroxy polymer is suspended in a suitable solvent which includes a swelling or solubilizing agent for the polymeric reaction product and a proton acceptor. Solvents which have been found suitable in serving both as a proton acceptor and a swelling or solubilizing agent include weak tertiary amine base as typified by pyridine, quinoline and isoquinoline and also N,N-dialkyl acylamides such as N,N-dimethylformamide and N,N-dimethylacetamide (hereinafter referred to as DMF and DMAC respectively), and mixtures thereof. Suitable swelling or solubilizing agents are generally solvents which are capable of dissolving polymeric esters. Typical examples of such swelling or solubilizing agents are ethyl acetate, ethyl formate, benzene, acetone, methyl ethyl ketone, and the like and mixtures thereof. Compounds which are suitable as proton acceptors are those, as previously described, which are capable of providing both swelling or solubilizing of the polymeric nitrite ester and also acting as a proton acceptor.

The amount of solvent which may be utilized to suspend the polyhydroxy polymer is not critical and may be varied over a relatively wide range. However, sufficient solvent should be used to avoid difficulty in handling the resulting viscous mixture. In general, it has been found that a minimum solvent to polymer weight ratio is 3:1, i.e., three parts by weight of solvent for each part of polymer.

In general, it is preferable that the solvent be capable of both swelling or solubilizing the resulting polyhydroxy polymer nitrite ester and also acting as a proton acceptor. The use of a single solvent, as opposed to use of a mixture of a proton acceptor with a swelling or solubilizing agent, provides process economies since it simplifies the recovery and the reuse of the solvent material. However, should a mixture of a proton acceptor with a swelling or a solubilizing agent be employed, it is necessary that the mixture contain at least one mole of the proton acceptor for each mole of the nitrosating agent, e.g., dinitrogentetroxide.

As stated, when a nitrite ester is nitrated or sulfated in accord with the invention, the product which is obtained is a novel polysaccharide or polyvinyl alcohol which contains a mixture of nitrite ester groups with sulfate or nitrate ester groups with the mixture of groups being substantially uniformly distributed among the polymer units in the polysaccharide or polyvinyl alcohol. These novel products are valuable intermediates in the preparation of a sulfate or nitrate ester of a polysaccharide or polyvinyl alcohol in which the sulfate or nitrate ester groups are substantially uniformly distributed among the polymer units in the polysaccharide or polyvinyl alcohol.

The use of a nitrite ester of a polysaccharide or a polyvinyl alcohol as a starting material in the preparation of another ester of a polysaccharide or a polyvinyl alcohol is of particular importance in the preparation of novel cellulose sulfate esters. By controlling the degree of substitution of the nitrite ester of cellulose employed as the starting material, the degree of substitution of the cellulose sulfate product may be likewise controlled. Thus, when the nitrite ester of cellulose has a degree of substitution of 2 to 3; the cellulose sulfate ester which is produced in accordance with the invention has a degree of substitution ranging up to about 1.1. However, when the nitrite ester of cellulose has a degree of substitution which is less than 2, the cellulose sulfate ester has a degree of substitution greater than about 1.1. In each case, the sum of the degree of substitution of the cellulose sulfate ester and the degree of substitution of the nitrite ester is equal to about 3.0.

A further aspect of the invention concerns novel water soluble sulfate esters of cellulose which have a degree of substitution of about 0.3 to about 1.0 with the sulfate ester groups being substantially uniformly distributed among the polymer units of the cellulose. The water solubility of these materials is quite surprising since cellulose sulfate esters, as prepared by prior art methods, are not water soluble unless the degree of substitution is in excess of 1.0. In the usage of these water soluble sulfate esters of cellulose, a further aspect of the invention concerns a thickened aqueous medium which contains water and a water soluble sulfate ester of cellulose having a degree of substitution of about 0.3 to about 1.0 with the sulfate ester groups being substantially uniformly distributed among the polymer units of the cellulose and the cellulose sulfate ester being present in an effective amount to thicken the aqueous medium.

A still further aspect of the invention concerns water insoluble esters of cellulose which are, however, highly swellable in the presence of water. These water insoluble cellulose sulfate esters have a degree of substitution of less than about 0.3 with the sulfate ester groups being substantially uniformly distributed among the polymer units of the cellulose. The water swellability of these materials is quite unusual. Due to the unusual properties of the water swellable esters of cellulose having a D.S. less than about 0.3, these materials have novel utilities in the preparation of absorbent materials, such as diapers, towels and the like.

A further aspect of the invention concerns nitrite esters of a polysaccharide or polyvinyl alcohol having a degree of substitution of less than about 2.0. In particular, the nitrite esters of cellulose having a degree of substitution of less than 2.0 are of unique value since they may be employed in forming cellulose sulfate esters, as described, having a degree of substitution of about 1.1 to 2.0 with the sum of the degree of substitution of the nitrite ester groups and the degree of substitution of the sulfate ester groups in the precursor mixed ester being equal to about 3.0.

A still further aspect of the invention concerns novel water soluble nitrate esters of a polysaccharide or a polyvinyl alcohol having a degree of substitution of less than 1.0 in which the nitrate ester groups are substantially uniformly distributed among the polymer units of the polysaccharide or polyvinyl alcohol. The properties of these materials are unique in that nitrate esters produced by prior art procedures are highly substituted and water insoluble.

As a corollary to my unique water soluble nitrate esters of a polysaccharide or a polyvinyl alcohol, a further aspect of the invention concerns a thickened aqueous medium containing water and a water soluble nitrate ester, as described, having a degree of substitution of less than 1.0. The nitrate ester groups are substantially uniformly distributed among the polymer units of the polysaccharide or polyvinyl alcohol and the water soluble nitrate ester is present in an effective amount to thicken the aqueous medium.

A still further aspect of the invention concerns an improved process for the preparation of nitrite esters of cellulose. As described, the usage of a nitrite ester intermediate of cellulose makes possible the preparation of novel cellulose esters, such as cellulose sulfate or cellulose nitrate, in which the properties of the final product may be attributed to the substantially uniform distribution of ester groups among the polymer units of the cellulose. It has been found that the nitrosation of cellulose with dinitrogentetroxide or nitrosyl chloride, and the subsequent sulfation as described previously, may be even further improved if the cellulose reactant is in an activated state or suitably activated. In accord with the improved process, the cellulose reactant is in a hydrated form and contains from about 4 to about 12 percent by weight of water with the water being substantially uniformly distributed throughout the cellulose reactant.

In using the hydrated cellulose as a reactant, the nitrosation reaction can be carried out in a shorter time with the use of essentially stoichiometric amounts of the nitrosation reactant. This produces a more homogeneous reaction mixture, a higher clarity product and, thus, permits easier separation of the product from the reaction mixture and reduces the need for filtration.

A still further aspect of the invention concerns a variation of my improved nitrosation process in which the cellulose reactant is substantially uniformly hydrated. In this variation, a hydrated cellulose which may contain in excess of about 4 percent by weight of water distributed substantially uniformly throughout the cellulose is washed with a highly polar aprotic solvent to reduce the water content of the cellulose to less than about 4 percent by weight. Surprisingly, it has been found that the cellulose remains in an activated state after washing with the aprotic solvent, even though the washed cellulose has a water content less than about 4 percent by weight. The washed cellulose can then be employed in the manner described previously for nitrosation with dinitrogentetroxide or nitrosyl chloride.

In a still further aspect of the invention, it has been found that the nitrite substituent groups present in nitrite esters of polyhydroxy polymers, e.g., cellulose, or in mixed nitrite:nitrate esters or nitrite:sulfate esters of a polyhdroxy polymer are surprisingly labile. Thus, unlike other nitrites, the nitrite substituent groups on the cellulose (or other polyhydroxy polymer) may be readily removed to form alkyl nitrites during formation of nitrate or sulfate esters of cellulose from cellulose nitrite esters with the alkyl nitrites being by-products to the formation of cellulose nitrate or cellulose sulfate esters.

In forming an alkyl nitrite ester as a by-product in accord with the invention, an alkyl alcohol is added to a reaction mixture containing a mixed nitrite:nitrate or a mixed nitrite:sulfate ester of a polysaccharide or a polyvinyl alcohol. Since the mixed ester is generally formed through addition of a nitrating or sulfating reagent, as described previously, to a reaction mixture formed in the production of the nitrite ester intermediate, dinitrogentetroxide may be liberated and be present in the reaction mixture. When alkyl alcohol is added, the alcohol reacts with both the free dinitrogentetroxide and the labile nitrite groups on the polysaccharide or polyvinyl alcohol. The reaction of the dinitrogentetroxide with the alkyl alcohol results in the formation of alkyl nitrite esters by a direct nitrosation which is comparable, in terms of mechanism, to reaction of dinitrogentetroxide with a polysaccharide or polyvinyl alcohol in forming the nitrite ester. However, reaction of the nitrite substituent groups on the polysaccharide or polyvinyl alcohol with the alkyl alcohol occurs through a transesterification reaction rather than a direct nitrosation. Although not bound by any theory, it appears that the transesterification reaction favors the production of the most stable nitrite ester in the system which, in this particular case, is the alkyl nitrite which is produced quantitatively.

Whatever the reaction mechanism may be, it is most important that both the free dinitrogentetroxide and the nitrite substituent groups on the polysaccharide or polyvinyl alcohol quantitatively form the same alkyl nitrite product so that the excess dinitrogentetroxide enters into the production of the valuable by-product alkyl nitrite.

As a suitable alkyl alcohol, various alkanols and alkanediols may be used, such as propanol, butanol, amyl alcohol, ethanediol, 1, 2-propanediol, etc. In addition, higher alcohols may be used such as decanol containing up to about 10 carbon atoms. Primary alcohols, such as butanol, secondary alcohols, such as isopropanol, and also tertiary alcohols, such as tertiary butyl alcohol are equally suitable for the reaction. In order to utilize the dinitrogentetroxide reagent quantitatively in the reaction, the alkyl alcohol reactant should be present in an amount of at least one mole of alkanol or one-half mole of alkenediol for each mole of dinitrogentetroxide which is initially added in forming the nitrite ester of the polysaccharide or polyvinyl alcohol intermediate with the alcohol being added after formation of the mixed polysaccharide or polyvinyl alcohol ester.

Since alkyl nitrite esters are relatively stable in comparison to the nitrite esters of polysaccharides or polyvinyl alcohol, the further reaction steps in forming the primary nitrate or sulfate ester product, i.e., neutralization, separation and isolation of the resulting nitrate or sulfate ester of the polysaccharide or polyvinyl alcohol, can be carried out without first removing the alkyl nitrite ester. Thus, for example, in forming a mixed nitrite: sulfuric acid ester of cellulose with subsequent addition of the required amount of alcohol, the resulting sulfuric acid ester of cellulose may be precipitated by addition of acetone to the reaction mixture followed by removal of the precipitate for further processing. The alkyl nitrite ester remains in the filtrate and both the solvents and the alkyl nitrite may be readily recovered by fractional distillation or any other suitable means.

Since the filtrate is acidic, it may be neutralized with a suitable base prior to distillation to minimize decomposition of the various compounds. As an additional way to minimize decomposition, the distillation may be carried out at a reduced pressure.

In separating the ester product, such as the sulfuric acid ester of cellulose, it is generally preferred to neutralize the entire reaction mixture without first isolating the ester product. This provides a large saving in the amount of solvent which is used and no decomposition of the alkyl nitrite by-product has been observed when the product recovery is carried out in this manner. Thus, after addition of the alkanol or alkanediol, a suitable base, such as the ammonium and N-substituted ammonium, alkali, or alkaline earth hydroxides, carbonates, or bicarbonates is added as an aqueous solution or as a suspension of an excess quantity of base in its saturated solution with continuous mixing of the reaction mixture during addition of the base. The preferred bases are the alkali carbonates and alkali bicarbonates which may be added also in the form of dry powders. To prevent any degradation of the polysaccharide ester product or polyvinyl alcohol ester product, e.g., the cellulose sulfate ester, the reaction mixture is preferably kept at a temperature of below about 15°-20° C. until the neutralization is completed.

If the solids concentration of the reaction mixture is sufficiently high and the concentration of water in the mixture is relatively low, the cellulose sulfate ester may be present in a wet solid form and may be readily removed. If, however, the cellulose sulfate ester is in the form of a paste after neutralization, a sufficient quantity of a water miscible solvent, such as acetone, methanol, ethanol, or isopropanol, is added to cause separation so that the product can be removed, pressed out, and dried or purified further. If the product is dried directly, the resulting product is a technical, relatively crude grade product which containes salt as the principal impurity. A purified product may be prepared by extracting the wet solids one or more times with an aqueous alcohol, such as methanol, ethanol, or isopropanol containing about 20–40 percent by weight of water, followed by drying of the product at an elevated temperature. Of course, it is also possible to extract the dried technical grade produce with aqueous alcohol to arrive at a refined grade.

The filtrate, as described above, may contain both solvents and also an alkyl nitrite and both the solvents and alkyl nitrite may be easily recovered by distillation. If a higher alkyl nitrite, e.g., in excess of about 7 carbon atoms, is produced as a by-product which contains a relatively high number of carbon atoms, part of the higher alkyl nitrite may remain with the solids because of its reduced solubility in aqueous alcohol. In this event, a final extraction may be carried out with anhydrous alcohol or with an alcohol containing less than about 20% of water. This will remove the higher alkyl nitrite more thoroughly and will result in obtaining higher yields during distillation. In addition, it is also possible to dry the solids in a closed system such that all absorbed solvents, including any retained alkyl nitrite, can be recovered.

A second by-product which may be formed in equivalent amounts is an inorganic nitrate, for example, sodium nitrate, if sodium hydroxide or sodium carbonate was used for neutralization. If it is not desired that an alkyl nitrite ester be produced simultaneously with production of the inorganic nitrate, an equivalent amount of water may be added to the reaction mixture instead of adding an alkyl alcohol. This will then result in the formation of equivalent amounts of inorganic nitrate and nitrite, such as sodium nitrate and sodium nitrite. Both salts will be in the filtrate and will remain in the residue after recovery of the solvents. The salts may be purified by crystallization or other known methods to provide salts of medium or high purity. However, if the salts are to be used as fertilizers, additional purification may not be necessary.

The first step of a process in accordance with one embodiment of this invention comprises nitrosating a polyhydroxy polymer suspended in a suitable solvent with dinitrogentetroxide, nitrosyl chloride or mixtures thereof to obtain the corresponding polyhydroxy polymer nitrite ester.

The nitrosating compound is used in the reaction mixture at a molar ratio of anhydroglucose or generally polymer unit to dinitrogentetroxide or nitrosyl chloride of about 1:0.1 to 1:3, resulting in a D.S. of 0.1 to 3. Since the reaction is quantitative, the D.S. approximately coincides with the molar amount of nitrosating agent used. If nitrosyl chloride is used in combination with DMF or DMAC, a 2.5 to 3.0-fold excess of the nitrosating reagent is required to attain these D.S.'s. Stated another way, one mole of dinitrogentetroxide or nitrosyl chloride is necessary to replace one mole of hydroxyl radical of the polyhydroxy polymer, and is nitrosyl chloride is used with an N,N-dialkyl acidamide as the proton acceptor, 2.5–3.0 moles of nitrosyl chloride are required.

The maximum D.S. for hexosans, such as cellulose, starch, guar and locust bean gums, mannans, and the like is about three; for pentosans, such as hemicellulose, and polyuronic acids, such as alginic and pectic acids, it is about two; and for polyvinyl alcohols the maximum D.S. is about one or less. Thus, the molar amount of dinitrogentetroxide necessary to obtain complete esterification for hexosans is about three moles per mole of anhydrohexose unit, for pentosans and polyuronic acids about two moles per mole of anhydropentose or uronic acid units, and for polyvinyl alcohols about one mole or less depending upon the degree of saponification of the starting compound. The same mole ratio amount of nitrosyl chloride is necessary for complete esterification of each of the hereinbefore described classes of polyhydroxy polymer unless DMF or DMAC is used as the solvent, in which case the amount has to be substantially tripled. An excess amount of the nitrosating compound beyond that necessary for complete esterification may be added with the only effect being an increased rate of esterification.

The nitrosation reaction is preferably carried out with constant agitation of the reaction mixture. It is necessary that the nitrosating compound be introduced into the polymer suspension under the exclusiion of moisture. It is preferably to cool the reaction vessel in an ice bath or the like since the reaction is moderately exothermic, and it is desirable to maintain the termperature of the reaction mixture below 50° C.

If maximum esterification is desired, completeness of the reaction is indicated by the formation of a clear solution or paste, while partial esterification is indicated by a swelling and/or partial dissolving of the product in the reaction mixture.

The polymeric nitrite esters are relatively sensitive products and decompose immediately upon addition of a protic solvent, such as water, methanol, ethanol, isopropanol, or the like in the presence of a mineral acid catalyst. This results in the regeneration of the undegraded polyhydroxy polymer starting material.

Since the novel polymeric nitrite esters of this process find their primary utility as intermediates in the production of other ester derivatives, such as polymeric nitrate and sulfate esters and the like, there is no need to isolate the nitrite esters as the reaction mixture may be used for those processes, as hereinafter described. However, the polymeric nitrite esters may be isolated by neutralizing the reaction mixture by the addition of a base, such as mono-, di-, and trialkylamines, pyridine, alkali or alkali earth metal hydroxides, carbonates, bicarbonates, or the like. The addition of such a base is necessary only if an N,N-dialkyl acylamide had been used as the proton acceptor since, during nitrosation with dinitrogentetroxide or nitrosyl chloride, an equimolar amount of nitric acid or hydrochloric acid is formed. If a weak tertiary amine base, such as pyridine or quinoline, had been used as the proton acceptor, the addition of a base is unnecessary since, then, the acid formed is neutralized by the tertiary amine base and cannot serve as a catalyst for the decomposition of the polymer nitrite.

The neutralized, or preferably slightly alkaline solution is then added to ice cold water with stirring to separate the polymeric nitrite ester as a fibrous material, which may be easily removed. Those products with a D.S. considerably below the maximum may be swellable or even soluble in water, in which case an alcohol is used in place of the water.

The isolated product is relatively unstable and for storage purposes it is preferred that it be solvated in a suitable solvent such as benzene, ethylacetate, ethylene dichloride, DMF, DMAC, or the like and stored at a low temperature, preferably below 10° C.

In forming a nitrate ester product, the second step of the process comprises heating the polymer nitrite ester solution in the presence of nitric acid with agitation at a temperature of 60°–110° C. for a period of 15 minutes to about two hours to obtain the corresponding polymer nitrate ester.

Although the polymeric nitrite ester solution used in step 2 is generally the reaction mixture formed in step 1, in which DMF or DMAC has been used as the proton acceptor and dinitrogentetroxide as the reagent in an amount sufficient for nitrosation to about the maximum D.S., the polymeric nitrite ester may be isolated after step 1 and then redissolved in one of the solvents, as stated above, and the corresponding amount of anhydrous nitric acid added. The use of the reaction mixture of step 1 for step 2 obviates the need for isolation of the polymeric nitrite ester as hereinbefore described. Also, the addition of nitric acid during step 2 is not necessary in this case since, during nitrosation with dinitrogentetroxide in DMF or DMAC, enough nitric acid is formed for the subsequent nitration.

Subsequent to heating, the polymeric nitrate ester is isolated by pouring the reaction mixture slowly and with agitation into two to five volumes of a water miscible protic solvent, such as methanol, ethanol, isopropanol, and the like, which splits off residual nitrite groups and separates the resulting product. The product is then filtered off, washed with fresh solvent and dried.

The resulting nitrate ester product is water soluble, and aqueous solutions of the ester tolerate relatively high concentrations of water miscible organic solvents such as the alcohols and ketones. Cellulose nitrate becomes water soluble if the D.S. exceeds about 0.5. To illustrate, if the D.S. of the cellulose nitrate ester is lower than about 0.5, the product can be highly hydrated but does not completely dissolve. Further, the solutions of the polymeric nitrate esters have a relatively high viscosity and owing to their solubility or improved hydration in water and aqueous organic solvents, their usefulness is enhanced.

To form the polymeric sulfate ester, step 2 as previously defined is omitted and alternatively, the next process step comprises sulfating the polymeric nitrite ester solution, preferably with a sulfur trioxide solvent complex, at a low temperature to obtain a polymeric mixed nitrite:sulfuric acid ester.

The polymeric nitrite ester solution preferably comprises the reaction mixture of step 1, in which a N,N-dialkyl acylamide has been used as the proton acceptor. The temperature of the reaction mixture should be maintained in the range from about 0° C.-25° C., and preferably 5°-15° C. to prevent depolymerization of the molecule during sulfation.

The preferred sulfating agent is sulfur trioxide which may be added to the reaction mixture in either its liquid or gaseous form or as a solution in an inert solvent such as carbontetrachloride. However, since the addition of sulfur trioxide is very exothermic and a low reaction temperature is critical to obtaining the desired viscosity in the product, the sulfur trioxide must be added slowly with stirring, while maintaining the reaction mixture in a cooling medium such as an ice bath.

In practice, it is preferred that the sulfating agent be first added to a solvent, preferably the same solvent as contained in the reaction mixture to facilitate solvent recovery, to form a complex which upon addition to the reaction mixture produces a less exothermic reaction. Examples of solvents capable of forming a complex with sulfur trioxide are DMF, DMAC, dioxane and pyridine. Generally, the mole ratio of the sulfur trioxide to the solvent in the complex is 1:1. However, it is preferable to use an excess of the solvent to obtain a suspension or solution of the complex in the excess.

The complex is slowly added to the reaction mixture with agitation and exclusion of moisture. The amount of sulfating agent to be added to the mixture is dependent upon the D.S. described in the resulting product. A low D.S. value ranging between 0.1 to 1.0 requires about 0.1 to about 1.0 mole of sulfur trioxide per mole of anhydroglucose unit. A D.S. value ranging from about 1.0 to about 2.0 requires about 1.0 to 4.0 mole of sulfur trioxide per anhydroglucose unit. A D.S. exceeding 2.0 is difficult under the reaction conditions, and a large excess of sulfur trioxide is required.

The addition of the sulfating agent to the polymer nitrite ester mixture forms a mixed polymeric nitrite:sulfuric acid ester. Although the polymeric nitrite ester with a maximum D.S. may be used for the sulfation to obtain products with a degree of sulfation of up to about 1.1, it is preferred to use the lower D.S. polymer nitrites for economic reasons and particularly where a D.S. of above about 1.1 is desired. Cellulose, for example, can be easily sulfated to a D.S. of between about 1 and 2 only when the degree of nitrosation is between about 2 and 1. However, if the degree of nitrosation drops considerably below about 1, sulfation becomes increasingly more difficult and incomplete and the distribution of the sulfate groups non-uniform. Generally, the higher the degree of sulfation desired, the lower may be the degree of nitrosation such that the mixed polymer nitrite sulfuric acid ester has a maximum D.S. In other words, the sum of the degree of nitrosation and the degree of sulfation should be about 3 for the hexosans, about 2 for pentosans and polyuronic acids, and about 1 or less for the polyvinyl alcohols.

The next step of the process comprises reacting the mixed polymeric nitrite:sulfuric acid ester with a protic solvent to obtain the corresponding polymeric sulfuric acid ester.

The addition of a protic solvent such as water, methanol and ethanol results in the production of the pure polymeric sulfuric acid ester. The protic solvent replaces the nitrite groups of the product with hydroxyl groups and is added in stoichiometric amounts or an excess thereof.

To isolate the polymeric sulfate ester product, two to four volumes of a water miscible solvent, i.e., acetone, is added to the mixture to separate the sulfated polymer therefrom. The ester is removed and washed with fresh solvent, and redissolved in ice water.

The next step of the process comprises neutralizing the polymeric sulfuric acid ester with a base to form a salt thereof.

The isolated polymeric sulfuric acid ester will degrade upon storage and therefore it is preferable to convert it to a neutral salt. The preferred bases for neutralizing the sulfate ester are the hydroxides, carbonates and bicarbonates of the alkali and alkaline earth metals, while ammonium hydroxide and the amines are likewise useable for this purpose. The resulting salt product is isolated by adding the neutralized mixture with agitation to a water miscible solvent such as acetone, methanol, ethanol, and isopropanol or vice versa. The isolated product may be washed with an aqueous solvent and dehydrated by washing with anhydrous solvent. The separated polymeric sulfate ester salt may then be removed and dried for storage.

Instead of neutralizing an aqueous solution of the isolated polymeric sulfuric acid ester, the polymeric sulfuric acid ester-protic solvent reaction mixture of the previous step may be neutralized directly to obtain the polymeric sulfate ester salt. In this case, the base may be added as an aqueous solution or in its dry form. In the neutralized mixture, the product may be present in wet, but solid, form and may be removed directly by centrifugation or filtration, pressed out, and dried to obtain a technical grade product which contains salt impurities. A pure grade or product is obtained by washing the wet product one or more times with aqueous alcohol prior to drying. If there is a relatively large amount of water in the neutralized mixture, the product may be too soft to be removed or it even may be partially dissolved. In this case, enough alcohol is added to harden the product somewhat or to precipitate it, so it can then be filtered off or centrifuged.

The product is water soluble and since it does not undergo depolymerization, a 1% aqueous solution produces a very viscous and stable solution. The sodium cellulose sulfate esters become water soluble if the D.S. exceeds about 0.3 and have viscosity measurement of as high as 8000-9000 cps.

As a result of this unique physical property, the products exhibit utility as thickening, suspending and emulsifying agents. Generally, the viscosity decreases somewhat as the D.S. increases simply because of the additional weight to the polymer. However, in the application in bone glue it is preferred to use a product having a D.S. of above 1.0 since in this particular use, best results are obtained with the higher D.S. products.

The following examples illustrate specific preferred embodiments of this invention and are not intended to be limiting. All ratios in the following examples as well as in the specification and in the appended claims are by weight unless otherwise indicated, and temperatures are expressed in degrees centigrade.

EXAMPLE I

A. Preparation of Cellulose Nitrite Ester from Cellulose 20 g. of Whatman cellulose powder, CF.II, was dried overnight at 110° C. and placed in a three neck, round bottom flask equipped with a mechanical stirrer and calcium chloride tube. 200 ml of N,N-dimethylformamide (DMF) was added to the cellulose powder and the mixture was stirred at room temperature. With exclusion of moisture, dinitrogentetroxide ($N_2O_4$) gas was slowly introduced to the mixture over a period of two hours. It was observed that the mixture thickened with about 7-8 g. of $N_2O_4$ and that a transparent viscous mixture without any essential development of color was obtained upon introducing approximately 15 g. of $N_2O_4$. After introduction of approximately 30 g. of $N_2O_4$, the mixture formed a bluish green viscous solution, and on further addition of $N_2O_4$, the color became a deep green while the viscosity appeared to remain constant.

To a sample of the three solutions, an excess of pyridine was added and the slightly alkaline mixture was poured with stirring into ice water. A fibrous precipitate was formed, removed, washed with ice water and pressed out, and the temperature was maintained at 0°-5° C. The fibrous precipitate of the first two samples was found to be swellable and that of the third sample was found to be soluble in common solvents for polymer esters including dimethylformamide, dimethylacetamide, benzene, acetone and ethyl acetate. Upon attempting to dry the fibrous precipitate, the product decomposed as indicated by the release of brown fumes. The resulting dried product was found insoluble in the above described common polymer ester solvents.

To identify the resultant products as cellulose nitrite esters and the degree of substitution or esterification (D.S.) thereof, the products were decomposed and cellulose and nitrous acid determinations were made. Products isolated from the above three solutions were washed with ice water and suspended in distilled water in a closed Erlenmeyer flask, acidified with sulfuric acid, and magnetically stirred at room termperature for 1 hr. The mixture was then neutralized with sodium hydroxide and the insoluble cellulose was regenerated, filtered off, washed with distilled water and dried in vacuo at 100° C. The filtrate was collected for testing, as hereinafter described.

The identity of the regnerated cellulose was determined by comparison of the regenerated cellulose with the starting material by IR spectrophotometry, negative nitrogen analysis and found identical by the Kjeldahl method, and the absence of carboxyl groups as determined by the method of Samuelson and Wennerblom described in "Methods in Carbohydrate Chemistry", Vol. III Cellulose, 1963, p. 34.

To determine the lack of depolymerization of the molecule during the reaction and during storage of the reaction medium, the viscosity of the regenerated cellulose from reaction mixtures kept over various periods of time, in cuprammonium hydroxide solution was compared with the viscosity of the starting material in the same solution at an identical 0.5% concentration. The viscosities were measured with a Cannon Fenske Viscometer at 25° C. The results of the tests are tabulated in the table on the following page.

| Material | Time and Temp. of Storage | Viscosity, Sec. |
|---|---|---|
| Starting Cellulose Control | | 28.8 |
| Regenerated Cellulose | 6 hr. 5° C. | 27.0 |
| Regenerated Cellulose | 30 hr. 5° C. | 28.8 |
| Regenerated Cellulose | 120 hr. 5° C. | 28.3 |
| Regenerated Cellulose | 288 hr. 5° C. | 27.8 |

The nitrite in the filtrate, as hereinbefore described, was determined by oxidation with permanganate solution to nitric acid. The presence of nitric acid subsequent to oxidation was established by its determination as nitron nitrate according to the method of Hick described in Analyst, Vol. 59, pp. 18-25 (1934).

The degrees of substitution were calculated from the weight of the cellulose and the amount of nitrous acid. The degree of substitution calculated for the first solution containing about 7-8 g. of $N_2O_4$ was 0.7; the second solution containing about 15 g. of $N_2O_4$ was 1.5 and for the third solution containing about 30 g. of $N_2O_4$ was 2.8.

Results substantially similar to those obtained above are obtained when the following starting cellulose materials are substituted for Whatman cellulose powder: cotton linter pulp, celluloses derived from wood or isolated from rice, corn, barley and oat hulls or from bagasse. However, if the foregoing starting materials are used, the amount of DMF used must be increased owing to the higher viscosities of the resulting product. Partially substituted celluloses, such as methyl or carboxymethyl cellulose can be used also with essentially similar results except that the amount of reagent required for full nitrosation is less because of the smaller number of free hydroxyl groups present. Likewise, results similar to those obtained above are obtained when the following solvents are substituted for N,N-dimethylformamide: N,N-dimethyl acetamide, pyridine, quinoline, and mixtures thereof, or mixtures of one or more of the foregoing solvents and benzene, ethyl acetate, or acetone. It was also found that the dinitrogentetroxide gas could be replaced by its liquid form or a solution thereof in one of the above solvents and by nitrosyl chloride to produce substantially similar results.

B. Preparation of Cellulose Nitrate Ester from Cellulose Nitrite Ester

A dry 500 ml. three-neck, round bottom flask was charged with 9 g. of Whatman cellulose powder, CF II, suspended in 300 ml. of DMF and solubilized by adding approximately 15 g. of dinitrogentetroxide gas to form cellulose nitrate ester. The cellulose nitrate ester solution was mechanically stirred and heated at 90° C. for 50 minutes, poured slowly and with agitation into about 6 volumes of methanol to form a precipitate, which was filtered, washed with methanol, and dried.

Upon analysis the precipitate was found soluble in water and upon IR analysis showed a strong absorption peak at about 1680 cm$^{-1}$, each test indicative of nitrate ester groups.

Nitrogen determinations by the Kjeldahl method indicated the presence of nitrogen from which a 0.5 degree of substitution was calculated.

The addition of 15 g. of anhydrous nitric acid or 24 ml. of acetic anhydride to the cellulose nitrite ester solution prior to heating revealed that the degree of substitution for the resulting cellulose nitrate ester was elevated to 0.8.

Results substantially similar to those obtained above are obtained when DMF is substituted by DMAC or by a mixture of DMF or DMAC and benzene or when methyl cellulose, caarboxymethyl cellulose or carboxyethyl cellulose is used in place of cellulose.

EXAMPLE II

A. Preparation of Hemicellulose Nitrite Ester from Hemicellulose

A 500 ml. three-neck round bottom flask equipped with a mechanical stirrer and calcium chloride tube was charged with 40 g. of hemicellulose extracted from corn hulls and suspended in 300 ml. of DMF. The suspension was mechanically stirred and under the exclusion of moisture, 58 g. of dinitrogentetroxide gas was slowly introduced to the mixture at room temperature to form a clear viscous solution of hemicellulose nitrite ester.

To a portion of the solution was added an excess of pyridine and the slightly alkaline solution was slowly poured with stirring into ice water to separate a fibrous precipitate. The precipitate was removed, washed with ice water and pressed out. The resulting precipitate was found soluble in common polymer ester solvents described in Example 1A. Upon drying, the precipitate decomposed releasing brown fumes.

Hemicellulose was regenerated for analysis by slowing adding a portion of the remaining hemicellulose nitrite ester solution to four volumes of methanol with agitation forming a precipitate which was filtered, washed with methanol, and dried. The precipitate was identified as hemicellulose by IR spectrophotometry and by negative nitrogen analysis by the Kjeldahl method.

The lack of depolymerization of the regenerated hemicellulose was determined by preparing 2% aqueous solutions of the regenerated product and the starting material and adjusting the pH of the solutions to 6.7 with a dilute sodium hydroxide solution. The viscosities of the two solutions were measured with a Cannon Fenske Viscometer at 25° C. The viscosity of the regenerated hemicellulose was observed to be 138.5 sec. and the starting material 146.2 sec.

To identify the product as the nitrite ester and to determine the D.S., an excess of triethylamine was added to the reaction mixture and the slightly alkaline solution was poured slowly and with stirring into ice water which resulted in the separation of hemicellulose nitrite ester. The hemicellulose nitrite was removed, suspended in water, and the mixture acidified with sulfuric acid and stirred for about 1 hour. Then it was neutralized with sodium hydroxide and the neutral solution was added to 4 volumes of methanol, wherein hemicellulose separated, and was removed, washed with methanol, dried and weighed.

The filtrate was collected, the methanol removed by concentration in vacuo, and the resulting aqueous nitrite solution was oxidized with a permanganate solution to form nitric acid, the presence of which was established by its determination as nitron nitrate according to the method of Hick described in Analyst, supra.

The degree of substitution was calculated by the weight of the hemicellulose and the amount of nitrous acid, and was found to be about 2.0. With less $N_2O_4$, the D.S. was correspondingly lower.

Results substantially similar to those obtained above are obtained when the following reagents are substituted for N,N-dimethylformamide: N,N-dimethyl acetamide, pyridine, quinoline and mixtures thereof, and mixtures of one or more of the above solvents and benzene, ethyl acetate, or acetone. Likewise, dinitrogentetroxide liquid or nitrosyl chloride can be substituted for the dinitrogentetroxide gas to produce substantially similar results.

Hemicellulose nitrate ester is prepared from the hemicellulose nitrite ester in the same manner as related in Section B of Example I.

EXAMPLE III

A. Preparation of Starch Nitrite Ester from Pregelatinized Starch

A 500 ml. three-neck round bottom flask equipped with a mechanical stirrer and calcium chloride tube was charged with 40 g. of pregelatinized starch and suspended in 300 ml. of DMF. Under exclusion of moisture, approximately 64 g. of dinitrogentetroxide gas was slowly introduced to the mixture at room temperature and the mixture was mechanically stirred to form a clear viscous solution of starch nitrite ester.

To test the resulting solution, an excess of pyridine was added to a portion of the solution and the slightly alkaline mixture was slowly poured with stirring into ice water to separate a fibrous precipitate. The precipitate was removed, washed with ice water and pressed out. The resulting precipitate was found soluble in the common polymer ester solvents described in Example IA. Upon drying, the precipitate decomposed releasing brown fumes, indicative of a nitrite. The dried precipitate was again tested for its solubility, and found to be insoluble in the common polymer ester solvents.

Another portion of the starch nitrite ester solution was slowly added to four volumes of methanol with agitation, and the precipitate was identified as starch by IR spectrophotometry and by negative nitrogen analysis by the Kjeldahl method.

The lack of depolymerization of the regenerated starch was determined by preparing a 1% aqueous solution of the regenerated product and comparing its viscosity against the starting material. The solutions were adjusted to a pH of 6.0 with a dilute sodium hydroxide solution and the viscosities of the two solutions were measured with a Cannon Fenske Viscometer at 25° C. The viscosity of the regenerated starch was observed to be 29.3 sec. as compared to 30.4 sec. for the starting material.

The product was identified as starch nitrite ester and its D.S. determined by the method described under Example II for hemicellulose. The degree of substitution was calculated by the weight of starch and the amount of nitrous acid, and found to be about 2.8. The D.S. was lower if a lower amount of dinitrogentetroxide was used for nitrosation.

Results substantially similar to those obtained above are obtained when the following starting materials are substituted for the pregelatinized starch: alginic acid, guar gum and locust bean gum or starch derivatives containing free hydroxyl groups, such as hydroxyethyl starch. Likewise, N,N-dimethyl acetamide, pyridine, quinoline and mixtures thereof, and mixtures of one or more of the above solvents and benzene, ethyl acetate, or acetone may be substituted for N,N-dimethylformamide to obtain substantially the same results. Further, nitrosyl chloride, liquid dinitrogentetroxide, or a solution of dinitrogentetroxide in one of the above solvents could be substituted for the dinitrogentetroxide gas and produce substantially similar results.

The starch and other polysaccharide ester solution was converted to the corresponding nitrate ester solution in a manner similar to Example IB.

EXAMPLE IV

A. Preparation of Polyvinyl Nitrite Ester from Polyvinyl Alcohol

To a dry 500 ml. three-neck round bottom flask, 10 g. of finely ground polyvinyl alcohol having a degree of saponification greater than 90% was suspended in 100 ml. of N,N-dimethylformamide. The mixture was mechanically stirred and under exclusion of moisture, dinitrogentetroxide gas was introduced. The vessel was cooled with cold water to keep the temperature at approximately 25° C. A clear viscous solution was obtained upon the addition of approximately 20 g. of dinitrogentetroxide gas.

Upon analysis, according to the methods described in Examples II and III, the resulting product was identified as polyvinyl nitrite ester having a degree of substitution of 0.8.

It was found that when the polyvinyl alcohol starting material had a degree of saponification less than 90% for example a product containing about 50% acetyl groups and 50% free hydroxyl groups, substantially the same results could be produced as obtained above, however the amount of dinitrogentetroxide gas required to solubilize the starting material was less.

The nitrite ester was converted to the nitrate ester in a manner similar to Example IB.

EXAMPLE V

A. Preparation of Sodium Alginic Acid Nitrate Ester 2 g. of alginic acid was suspended in 80 ml. of DMF and solubilized by 4.5 g. of dinitrogentetroxide gas according to the procedure of Example III. The solution was heated at 90° for 40 minutes and added slowly, with agitation, to 3 volumes ethanol to precipitate alginic acid nitrate ester. The isolated precipitate was resuspended in water and neutralized with sodium hydroxide. The neutralized solution was then added slowly to 3 volumes of ethanol to precipitate sodium alginate nitrate ester.

Results substantially similar to those obtained above are obtained when pectic acid is substituted for alginic acid. The substitution of potassium hydroxide, calcium hydroxide, magnesium hydroxide and ammonium hydroxide for the sodium hydroxide results in the corresponding potassium, calcium, magnesium and ammonium salts of the polyuronic nitrate esters.

EXAMPLE VI

A. Preparation of Cellulose Sulfuric Acid Ester 10 g. of cotton linter pulp having a high degree of polymerization was suspended in 500 ml. of DMF and reacted with dinitrogentetroxide to form the nitrite ester thereof with the maximum D.S. in accordance with Example IA. 40 ml. of DMF containing 3.5 g. of sulfur trioxide was added to the nitrite ester mixture dropwise over a period of about 40 minutes maintaining the temperature of the solution at 15° C., with vigorous agitation to form a viscous solution. 20 ml. of water was added to the viscous solution and it was then poured slowly and with vigorous agitation into 3 volumes of acetone to precipitate cellulose sulfuric acid ester, which precipitate was kneaded, washed and acetone. and redissolved in ice water.

B. Preparation of Sodium Cellulose Sulfate Ester

The solution prepared in accordance with Example VIA was neutralized by the addition of sodium hydroxide to a pH of about 8.0 to form a viscous solution of sodium cellulose sulfate ester. The solution was added slowly and with agitation to 3 volumes of acetone to precipitate and isolate the product. The precipitated product was kneaded, collected, washed with fresh acetone and dried. Upon analysis, the yield of sodium cellulose sulfate ester was 13.9 g. having a degree of substitution of 0.65, and a viscosity of 6500 cps. as a 1% aqueous solution.

The viscosity was measured with a Brookfield Viscometer, Model LVT, at 12 RPM and 25° C. To determine the degree of substitution, a 0.4 g. aliquot of the product was dissolved in 20% aqueous hydrochloric acid and heated for 15 hours at 100° C. A dark brown solution was formed and filtered. To the filtrate, an excess of barium acetate was added to precipitate sulfuric acid as barium sulfate. The barium sulfate was dried and weighed and the degree of substitution calculated therefrom.

Results substantially similar to those obtained above are obtained when the cotton linter pulp starting material is replaced by cellulose from other sources and/or having a lower degree of polymerization, hemicellulose, gum arabic, starch, alginic acid, guar gum, locust bean gum and polyvinyl alcohol. Other solvents capable of forming a complex with sulfur trioxide and which may be substituted for DMF in the DMF-sulfur trioxide complex are N,N-dimethyl acetamide, pyridine, trialkylamine, dimethylsulfoxide and dioxane. Likewise, the sulfur trioxide may be added to the solution in the form of a liquid or a gas, or diluted with an inert solvent such as carbontetrachloride though the reaction is highly exothermic and the use of an ice bath is necessary.

When the above procedure was repeated and the amount of sulfur trioxide was reduced to 2.5 g., the resulting product had a degree of substitution of about 0.5 and a viscosity of about 6000 cps. The yield was reduced only slightly to 13.4 g.

An increase of the sulfur trioxide to about 4–5 g. and about 6–7 g. resulted in D.S.'s of about 0.7–0.9 and about 1.0–1.1 with viscosities of about 6000–8000 cps. and about 3000–4000 cps., respectively. However, a further increase of the sulfur trioxide did not result in D.S. values of much above 1.0–1.1 under these conditions.

Similar results were obtained when cellulose nitrite ester with a D.S. of 2.4–2.5 was used.

D.S. (Degree of sulfation) values of 1.2–1.3 and about 1.5–1.6 were obtained by using a cellulose nitrite ester having a D.S. of about 1.7–2.0 and about 1.4–1.6 and increasing the amount of sulfur trioxide to about 8–10 g. and 12–14 g., respectively. The viscosities of 1% aqueous solutions of the products were about 1500–2000 cps.

and about 800–1500 cps., respectively. Similar results were obtained with starch, guar and locust bean gums, and with hemicellulose. Also, methyl cellulose with a D.S. of about 1.0–1.5, carboxymethyl cellulose, hydroxy ethyl starch, acetylated alginic and pectic acids (with a degree of acetylation of below about 1.5) and hydroxypropyl guar were found equally suitable for nitrosation and subsequent sulfation. However, the amount of reagent necessary for full nitrosation was based only on the number of free hydroxyl groups.

When cotton linter cellulose with a lower degree of polymerization was used, the D.S.'s were similar but the viscosities were correspondingly lower. Similarly, cellulose from other sources generally produced products with lower viscosities.

EXAMPLE VII

Cellulose (25 g.) was suspended in 1000 ml. DMF and about 38 g. $N_2O_4$ were introduced to obtain cellulose nitrite ester. A solution of a calculated amount of DMF-$SO_3$ complex in DMF was then slowly added with stirring and cooling to result in a degree of sulfation of about 0.8.

At this stage, a small portion of the mixture was removed, and, after removal of the nitrite groups and neutralization, the product was dialyzed, isolated, and analyzed. The D.S. was found to be 0.8.

The main portion was mixed with the stoichiometric amount of methanol required for the quantitative removal of the nitrite groups, and subsequently another portion of DMF-$SO_3$ complex, which theoretically was sufficient to increase the D.S. to about 2.0, was added over a period of 2 hours. After a total reaction period of about 3 hours, the mixture was neutralized and the product isolated as described above, dialyzed, and its D.S. determined. The D.S. calculated was 0.8 indicating that no further substitution had occurred after removal of the nitrite groups.

Similar results were obtained with guar and locust bean gums. This illustrates that sulfation under these conditions does not occur without the prior nitrosation step of this invention.

EXAMPLE VIII

To test the compatibility of the various sodium cellulose sulfate esters of this invention with metal ions, 1% aqueous solutions of the esters were mixed with the same volume of a 20% salt solution. In cases were 20% was above saturation, a saturated salt solution was used.

Products at all D.S. levels were compatible, i.e., no precipitation or gelling occurred, with ammonium sulfate, sodium chloride, potassium chloride, magnesium chloride, calcium chloride, calcium hydroxide, strontium chloride, strontium hydroxide, aluminum sulfate, sodium aluminate, zinc sulfate, sodium zincate, nickelous sulfate, cobaltous sulfate, cupric sulfate, cadmium chloride, ferrous sulfate, chromic chloride, lead acetate, mercuric acetate, silver nitrate, stannous chloride, and sodium stannite.

As a simple test for determining compatability with metal ions, a 2% solution of the cellulose sulfate in an aqueous medium may be admixed with a 2% potassium chloride solution on an equal volume basis after heating of both solutions to a temperature of about 80° C. After mixing, the mixture may be allowed to cool. The compatability of the cellulose sulfate with potassium ions is shown by the absence of a precipitate and the absence of gelation.

Sodium cellulose sulfate esters with a D.S. of about 1.3 and lower were compatible also with barium acetate, barium hydroxide, cerous chloride, and ferric chloride.

In most cases, the solutions could be saturated with the salt without causing precipitation or gelation.

EXAMPLE IX

A. Thickened Rubbing Alcohol Composition

A thickened rubbing alcohol having the following composition is prepared:

| Component | % by Weight |
|---|---|
| Cellulose Nitrate Ester | 5.0 |
| Water | 25.0 |
| Ethyl Alcohol | 70.0 |

The thickened rubbing alcohol exhibits a desired increased viscosity which tends to slow down evaporation of the alcoholic solution, prolong skin contact and thereby aid absorption.

EXAMPLE X

A. Non-running Glue

| Component | Amount by Weight |
|---|---|
| Bone Glue | 150.0 g. |
| Sodium cellulose sulfate | 5 g. |
| Water | 1000 g. |

This improved glue exhibits a higher viscosity tending to retard running of the glue, particularly on vertical surfaces. The particular composition exhibited a viscosity of 1000 cps. at 25° C. and about 300 cps. at 50° C. and did not interfere with or change the properties of the bonding glue.

Among the other utilities for my cellulose sulfate products are their application in oil well drilling mud as a suspending agent, in secondary oil recovery through water flooding as a thickener of the water phase, in cosmetics as an emulsifier and emollient, in food products as a thickener and stabilizer, in cleaning compositions as a stabilizer and thickener, in wax emulsions, paints, and photographic emulsions, e.g., for protein reactivity, etc.

EXAMPLE XI

Utilizing the process of the invention as described above, esters of polyhydroxy polymers such as polysaccharides, polyvinyl alcohols, and partially substituted etherified or esterified polysaccharides and polyvinyl alcohols which still contain a substantial number of free hydroxyl groups are prepared and the following specific products are obtained thereby:

A. Nitrite esters of polysaccharides, polyvinyl alcohols, polysaccharides partially substituted with stable radicals, and polyvinyl alcohols partially substituted with stable radicals.

B. Nitrite esters of starch, guar gum, locust bean gum, hemicellulose, gum arabic, mannan, alginic acid and pectic acid having a D.S. between 0.1 and the maximum.

C. Nitrite ester of cellulose having a D.S. between about 0.1 and 2.0.

D. Nitrite ester of cellulose having a D.S. between 2.0 and 3.0.

E. Water soluble nitrite esters of polysaccharides and polyvinyl alcohols having a D.S. of less than 1.0.

F. Sulfuric acid esters of polysaccharides and polyvinyl alcohols and salts thereof with a D.S. of below 2.0 and with substantially uniform distribution of sulfate groups over the macromolecule.

G. Sulfuric acid esters of guar gum and locust bean gum having a D.S. of between 1.0 and 2.0.

H. Sulfuric acid esters of cellulose having a D.S. of between 1.0 and 2.0.

I. Water soluble sulfuric acid esters of cellulose having a D.S. between 0.3 and 1.0.

J. Sulfuric acid esters of cellulose having a D.S. between 1.0 and 1.3 the aqueous solutions of which are compatible and non-gellable in the presence of potassium, barium, strontium, cerous, aluminum, and ferric ions.

K. Sulfuric acid esters of cellulose having a D.S. of less than 2.0 and with substantially uniform distribution of sulfate groups over the macromolecule, the aqueous solutions of which are compatible and non-gellable in the presence of potassium, strontium and aluminum ions.

As stated previously, a further aspect of the invention involves the use of an activated cellulose polymer in the formation of a nitrite ester. This aspect of the invention is illustrated in the following Examples in which all parts and percentages are by weight unless otherwise indicated.

EXAMPLE XII

Cotton linter pulp was dried at 100° to 110° C. in vacuo over $P_2O_5$ for 5 hours; a dried 20 g. portion was placed in a three-neck round bottom flask provided with a calcium chloride tube, a strong stirrer, and a dropping funnel, and 1 liter of DMF was added. An amount of 30 g. of $N_2O_4$ then was introduced with stirring over a period of about 30 minutes while the temperature of the mixture was kept below about 30° C. by cooling in a cold water bath. The mixture thickened, but the reaction was incomplete even after mixing for several hours indicated by the presence of haze and apparently unreacted fibers. The addition of another 3 g. of $N_2O_4$ did not result in a substantial improvement.

In isolating and analyzing the resuting cellulose nitrite ester, to a small portion of the mixture was added an excess of pyridine. The slightly alkaline mixture was added to ice water, the precipitate collected, washed with ice water, and pressed out while the temperature was kept at about 0° C. The material was redispersed in distilled water in a closed Erlenmeyer flask and acidified with sulfuric acid. After stirring magnetically for about 1 hour, the mixture was neutralized and the regenerated cellulose removed, washed, dried, and weighed. The filtrate was collected quantitatively and the nitrite determined by oxidation with permanganate to nitric acid. The presence of nitric acid subsequent to oxidation was established by its determination as nitron nitrate according to the method of Hick described in Analyst, Vol. 59, page 18-25 (1934). The degree of nitrosation was found to be about 2.7-2.8.

The cellulose nitrite reaction mixture prepared from 20 g. of cellulose and 30 g. $N_2O_4$ was sulfated by the slow addition (about 30 min.) of a solution of DMF-$SO_3$ complex (about 6 g. $SO_3$) in DMF. The reaction was carried out with strong stirring and under exclusion of moisture, and the temperature was kept below about 20° C. The mixture remained hazy and still contained fibers even after mixing for about 1-2 hours. The reaction mixture was then transferred to a mixer, diluted with about 500 ml. of water, and adjusted to a pH of 7-8 by the slow addition of sodium carbonate solution. During neutralization, the temperature of the mixture was kept below 20°-25° C. by the addition of ice. Enough isopropanol was then added to separate the product, and the product was pressed out, washed twice with aqueous isopropanol, pressed out again, dried in vacuo at 100° C., and milled. The product had a D.S. of about 0.6 and a 1% aqueous solution a viscosity of about 3000 cps. (Brookfield Viscometer, LVT Model, 60 RPM) but was somewhat hazy and contained fibers.

In another experiment, 20 g. of anhydrous cotton linter pulp was treated as described above, but only about 15 g. of $N_2O_4$ was used for the nitrosation to result in a D.S. of about 1.5 and an amount of DMF-$SO_3$ complex containing about 12 g. of $SO_3$ for the subsequent sulfation. The results were similar to those above. The cellulose sulfate had a D.S. of about 1.5, and a 1% aqueous solution had a viscosity of about 500 cps. but was hazy and contained fibers.

Essentially similar results were obtained when wood cellulose, cellulose from vegetable hulls or bagasse, and chemically treated and degraded cellulose, such as Whatman Cellulose Powder were substituted for the cotton linter pulp. However, it appeared that the reaction with Whatman Cellulose Powder proceeded more smoothly and that a solution of its final sulfated product was the least hazy and contained a lesser amount of fibers than those produced from other cellulose types.

Substitution of the DMF in the reaction medium by DMAC or pyridine or mixtures of these compounds did not essentially change these results. Also, no essential differences were noticed when the $SO_3$ was used as a complex with other solvents, such as DMAC, dioxane, DMSO, and the like, or when NOCl was used instead of $N_2O_4$ provided, however, that the molar amount of NOCl was increased 2.5 to 3 fold.

EXAMPLE XIII

Cotton linter pulp as described in Example XII was suspended in water and mixed in a Waring Blender for 2 min., pressed out, washed with DMF, and pressed out again. The cellulose then had a water content of about 8-10%. A portion of 20 g. of this cellulose then was nitrosated with 30 g. of $N_2O_4$ as described above. The resulting solution was clear and did not contain fibers after a reaction time of 20-30 min., and no excess of $N_2O_4$ was required to obtain a quantitative reaction. The sulfation was carried out as described above and resulted in products forming perfectly clear solutions that did not contain fibers.

Similar results were obtained when the residual water content was 5% and 2% or when cotton cellulose was replaced by wood cellulose or cellulose from bagasse or chemically treated cellulose.

When the amount of DMF-$SO_3$ complex added was that calculated to produce a D.S. of below about 0.3-0.4, the resulting product was insoluble but highly swellable in water.

EXAMPLE XIV

Cotton linter pulp was hydrated by treatment with water in a Waring Blender as described above. The cellulose then was pressed out and divided into 4 portions. One portion was dried in vacuo at 30°-40° C. with continuous mixing down to a water content of about 20%. The other three parts were dried under the same conditions to 8–10%, 4–5%, and 1–2% water, respectively. For the last sample the temperature was somewhat increased. Amounts of 20 g. of each of the parts were nitrosated as described above with 30 g. of $N_2O_4$. The reactions with samples containing 8–10% and 4–5% moisture proceeded smoothly and were complete after about 20–30 minutes forming clear, viscous solutions. The cellulose containing 20% moisture required about 35 g. $N_2O_4$ and formed a clear solution soon after the 5 g. excess has been added. The cellulose portion containing 1–2% moisture required a long time of mixing and, even after the addition of a moderate excess, remained somewhat hazy and contained fibers.

Subsequent sulfations using DMF-$SO_3$ complex containing about 6 g. of $SO_3$ in each case resulted in cellulose sulfates with a D.S. of about 0.6 producing sparkling clear solutions in water when celluloses with moisture contents of 20%, 8–10%, and 4–5% were used initially. Solutions of the reaction product from cellulose with the lowest moisture content, however, were somewhat hazy and appeared to contain fibers.

Similar results were obtained when cotton linter pulp was replaced by wood cellulose or cellulose from vegetable hulls or bagasse, or when the DMF was substituted by DMAC, or when instead of the DMF-$SO_3$ complex, a complex with dioxane, DMAC, DMSO, or the like was used.

In another identical experimental series, where 20 g. portions of cellulose were nitrosated with about 20 g. of $N_2O_4$ (about 25 g. of $N_2O_4$ required for the cellulose containing about 20% moisture) and sulfated with DMF-$SO_3$ complex containing about 10–12 g. of $SO_3$, products with D.S. values of 1.1–1.2 were obtained, but otherwise results were similar.

The nitrosation and subsequent sulfation proceeded similarly smooth and resulted in sulfated products forming clear aqueous solutions when a commercial cotton linter pulp or wood cellulose with moisture contents of between about 4–12% was used directly. If 5%, 10%, or 20% water was added to anhydrous cellulose at once just before the reaction, results were similar to those obtained under Example XII with anhydrous cellulose.

EXAMPLE XV

Five samples of cotton linter pulp (20 g. each) were nitrosated as described above with about 30 g. of $N_2O_4$ each and then sulfated with DMF-$SO_3$ complex containing the theoretical amounts of $SO_3$ calculated for D.S. values of about 0.4, 0.6, 0.8, 1.1, and 1.6. After neutralization and isolation, the D.S. values of the products were found to be about 0.4, 0.6, 0.8, 1.1, and 1.1, respectively. The same D.S. values of about 1.0–1.1 were obtained also when the amount of $N_2O_4$ was reduced to 25 g. or about 20 g. and the $SO_3$ was calculated for a D.S. of about 1.1 and 1.6.

Cotton linter pulp (20 g.) which was nitrosated with 14 to 15 g. of $N_2O_4$ produced, after sulfation with a theoretical amount or a moderate excess of $SO_3$, a product with a D.S. of about 1.5 to 1.6. If the $N_2O_4$ was increased to 17 to 18 g., a theoreticl amount or an excess of $SO_3$ produced a D.S. of 1.3 to 1.4. However, if for the nitrosation about 25 g. of $N_2O_4$ was used, theoretical amounts of $SO_3$ was sufficient to produce D.S. values of between about 0.5 and 1.1. If less than about 10 g. of $N_2O_4$ was used for nitrosation, no complete sulfation was attained with DMF-$SO_3$ complex even when used in moderate excess. Substantially similar results were obtained when, instead of cotton linter pulp, wood cellulose or bagasse was used.

EXAMPLE XVa

Carboxymethyl cellulose (10 g.) with a D.S. of about 1.0 was suspended in about 500 ml. DMF, and 7.5 to 8.0 g. $N_2O_4$ was introduced under exclusion of moisture and with strong agitation. The mixture formed a light green, viscous solution of carboxymethyl cellulose dinitrite ester.

For the isolation and identification of the ester, the same procedure was used as described under Example 1 for cellulose nitrite ester. If less $N_2O_4$ was used for the nitrosation, the degree of nitrosation was correspondingly lower.

Similar results were obtained when methyl cellulose with a D.S. of 1.0 and 1.5, hydroxypropyl cellulose with a D.S. of 0.8, acetyl alginic acid esters with a D.S. of 0.5 and 0.8, hydroxyethyl starch with a D.S. of about 0.2, partially hydrolysed polyvinyl acetate with a D.S. of 0.4, acetyl pectic acid ester with a D.S. of 1.2, hydroxyethyl guar and locust bean gums with a D.S. of about 0.4 and 0.7, hemicellulose nitrate ester with a D.S. of about 0.3 (as described in the German Offenlegungsschrift No. 2,120,964), polyvinyl alcohol sulfuric acid ester with a D.S. of 0.3, starch phosphate, carrageenan (free acid), xanthan gum (free acid), or gum karaya were nitrosated under similar conditions with stoichiometric amounts of $N_2O_4$ to result in complete or partial esterification of the free hydroxyl groups.

Similar results were obtained when the DMF was replaced by DMAC, pyridine, isoquinoline, quinoline, and the like, or when NOCl instead of $N_2O_4$ was used provided that its molar amount was essentially tripled. Also, the reaction medium could contain substantial quantities of an inert solvent, such as ethyl acetate, ethyl formate, benzene, toluene, ethylene dichloride, acetone, methylethyl ketone, and the like, without substantially changing the reaction.

EXAMPLE XVI

DMF (100 ml) was poured into a 250 ml two-neck round bottom flask equipped with calcium chloride tube and magentic stirrer. Then, 23 g. of $N_2O_4$ (¼ mole) was added with stirring and cooling which resulted in the formation of a deep green solution. To this solution, 12 g. absolute ethyl alcohol (about ¼ mole) was added solwly with stirring. During addition of the last ml, the solution became light yellow indicating complete consumption of the $N_2O_4$. Then, the solution was neutralized by the addition of pyridine and subjected to fractionated distillation. The first fraction was collected in a flask cooled with acetone-dry ice and consisted of about 18 g. of a yellowish liquid having a boiling point of 17°–18° C. No ethyl alcohol was recovered during distillation.

Using the same conditions as in Example XVI, the ethyl alcohol was replaced by propanol, isopropanol, butanol, isobutanol, tertiary butyl alcohol, amyl alcohol, isoamyl alcohol, and hexy alcohol and ¼ mole ethylene glycol. On fractionated distillation, the corresponding nitrite esters were recovered in 80–90% yields with boiling points of about 57° C., 45° C., 77° C., 68° C., 63° C., 104° C., 99° C., 130° C., and 98° C., respectively. In no case was any alcohol recovered.

In another series of experiments, 15 g. of a low D.P. cellulose was suspended in the 100 ml of DMF before the $N_2O_4$ was added. Addition of 23 g. of $N_2O_4$ with strong stirring resulted in a cellulose trinitrite ester solution. To this solution, alcohol under conditions and in amounts as described above (1 mole alcohol or 0.5 mole diol per mole $N_2O_4$) was added. Free cellulose separated and was removed. The filtrate was neutralized and distilled as described above and the corresponding alkyl nitrites were obtained in yields of 80-85% of the theory. Similar results were obtained when, instead of cellulose, stoichiometric amounts of methyl cellulose, starch, alginic acid, or polyvinyl alcohol were used.

In a third experimental series, to cellulose trinitrite ester solutions obtained under conditions and in amounts as described above were added slowly and with continuous stirring amounts of $DMF-SO_3$ complex to result in mixed cellulose nitrite sulfuric acid esters having degrees of sulfation of about 0.4, 0.8, and 1.1. To these ester solutions, alcohol was added under conditions and in amounts as described above, the cellulose sulfuric acid ester preciptated by the addition of a sufficient amount of acetone and removed, and the filtrate neutralized with pyridine and subjected to fractionated distillation. The corresponding alkyl nitrites were recovered in a purity and in yields similar to those obtained from cellulose trinitrite ester solutions above.

EXAMPLE XVII

Cotton linter pulp (400 g.) having a moisture content of about 5-6% was mixed with 2 l. of DMF in a double planetary mixer with cooling and under exclusion of moisture, and 600 g. of $N_2O_4$ was added over a period of about 30 minutes to result in a cellulose trinitrite ester. Then, a $DMF-SO_3$ slurry in DMF containing about 200 g. of $SO_3$ was added slowly over a period of about 30 minutes and mixing continued for another 10-15 minutes. An amount of 485 g. of isobutyl alcohol was added slowly, and the mixture was neutralized (pH 7-8) by the addition of an aqueous solution of sodium carbonate or a slurry of sodium carbonate in a saturated solution or by the addition of dry sodium carbonate. Good and thorough mixing was required for this neutralization step, and generally the presence of water produced better results. The temperature of the reaction mixture was maintained below about 20° C. throughout the reaction until neutralization was complete, and up to the neutralization step, the reaction was carried out under exclusion of moisture. The neutral mixture was then pressed out or centrifuged, and if the solids were too soft to be pressed out, some isopropanol was added to harden them sufficiently. The solids were suspended to about 60-70% aqueous isopropanol, pressed out again, dried, and milled. For higher purity, the solids were suspended in aqueous isopropanol a second and, if necessary, a third time before final drying and milling.

The filtrates were combined and subjected to fractionated distillation for solvent recovery. One of the fractions distilled at about 66°-67° C. and was identified as isobutyl nitrite, the yield being over 80%. The brown, crystalline residue from distillation contained the theoretical amount of sodium nitrite. An aliquot of it was purified by recrystallization.

In other identical experiments, the isobutyl alochol was replaced by n-propanol, amyl alcohol, and ethylene glycol. Instead of isobutyl nitrite, the corresponding nitrite esters of n-propanol, amyl alcohol, or ethylene glycol were recovered, but otherwise results were similar. In another similar experiment where the isobutanol was replaced by an equivalent amount of water, similar results were obtained, but the residue from the solvent recovery contained equivalent amounts of sodium nitrite and sodium nitrate in theoretical yields. Part of the residue was recrystallized to result in a purified salt mixture.

The sodium cellulose sulfate had a D.S. of 1.0-1.1, and a 1% aqueous solution had a viscosity of 1500-2000 cps.

In another experimental series, products were obtained under similar conditions, but the amount of $SO_3$ used for the sulfation was reduced to obtain products with D.S. values of about 0.4, 0.6, and 0.9. These D.S. values were attained with the theoretically calculated amounts of $SO_3$, and 1% aqueous solutions of the products had viscosities ranging between about 5000 and 2000 cps. In another experiment, the amount of $N_2O_4$ was reduced to about 300 g. and that of $SO_3$ increased to about 300 g. to result in sodium cellulose sulfate esters with a D.S. of 1.5-1.6 having 1% aqueous viscosities of about 600-700 cps.

Other cellulose materials, such as wood cellulose or cellulose from vegetable hulls were used with equal success, but the final products had a somewhat lower solution viscosity than those from high D.P. cotton linter pulp. Also, neutralization could be carried out equally well with carbonates, bicarbonates, and hydroxides of the other alkali metals, such as lithium and potassium, of alkali earth metals, such as magnesium and calcium, and of manganese, cobalt, and nickel and with ammonium hydroxide and amines. In the case of the alkali metals, carbonates and bicarbonates are preferred to the hydroxides because of the high alkalinity of the hydroxides and the danger of degradation.

Also an integral part of my invention is the process of making films, fibers, and other shaped articles by (1) preparing a solution of paste containing the labile nitrite ester of one or more polyhydroxypolymers or a solution or paste of both one or more polyhydroxypolymer nitrite esters and one or more polymers lacking hydroxyl groups and (2) contracting said solution or paste with a protic solvent in the presence of an acidic catalyst to cause (a) regeneration of the polyhydroxypolymer and, essentially simultaneously, (b) separation of both the regenerated polyhydroxypolymers and the polymers lacking hydroxyl groups in such a manner that films, fibers, or other shaped articles are obtained.

The first step of the process consists of making the nitrite ester of the polyhydroxypolymer or polyhydroxypolymer mixtures as previously described. As the polyhydroxy compound, any polymer containing a substantial number of hydroxyl groups is suitable. This includes polysaccharides typified by cellulose irrespective of its source, alginic acid, pectic acid, pectin, hemicellulose, gum arabic, guar gum, locust bean gum, gum karaya, and the like, polysaccharide derivatives still containing a substantial number of hydroxyl groups as typified by carrageenan and other polysaccharide sulfates, methylcellulose, carboxyalkylcellulose, hydroxyalkylcellulose, hydroxyalkylguar and other polysaccharide ethers, partially acetylated or generally esterified polysaccharides, partially nitrated or sulfated polysaccharides such as described previously, and the like, and synthetic polyhydroxypolymers typified by polyvinylalcohols with various degrees of saponification and copolymers containing vinylalcohol.

To the suspension of the polyhydroxypolymer(s) in one of the specified solvents or solvent mixtures, enough dinitrogentetroxide and/or nitrosylchloride is added in gaseous or liquid form or as a solution preferably in one of the previously mentioned solvents to obtain a highly esterified nitrite ester of the polyhydroxypolymer(s). The reaction temperature should be maintained below about 50° C. and preferably below about 30° C. If the temperature increases to above about 60° C. over an extended period of time, some nitration of the polyhydroxypolymer may occur. This, however, may not have any disadvantageous consequences in the subsequent film or fiber formation, and, in some instances, it may be even desirable.

Films, fibers, and other shaped articles of the unmodified polyhydroxypolmyer(s) are obtained by bringing the paste or solution of the nitrite ester(s) into the desired shape and then contacting it in the presence of an acidic catalyst with a protic solvent in which the resulting polyhydroxypolymer(s) is (are) insoluble. Films, for example, can be made by spreading the solution on a glass plate and treating it with a protic solvent while fibers are obtainable by extruding the solution into the protic solvent. The shaped objects then may be immersed in and washed with more solvent and dried. To neutralize residual catalyst, a small amount of a base, such as alkali or ammonium hydroxides or an amine, may be added to one of the washes if so desired.

Although it is possible to first isolate the polymeric nitrite ester and then redissolve it for the purpose of film and fiber formation, it is preferred to use the reaction solution containing the nitrite ester directly. The preferred acidic catalyst is a mineral acid, such as hydrochloric, sulfuric, nitric, phosphoric acids, and the like, however, relatively strong organic acids are suitable also. If an N,N-dialkylacylamide had been used as the proton acceptor for nitrosation of the polyhydroxypolymer, the nitric acid and/or hydrochloric acid formed simultaneously as a by-product is sufficient to serve as a catalyst. However, if a weak tertiary amine had been used for this purpose, enough catalyst should be added to make the mixture acidic. The catalyst must be anhydrous to avoid removal of nitrite groups prior to the treatment with the protic solvent. Of course, a sufficient amount of catalyst may be added to the protic solvent instead of to the nitrite ester solution, and film or fiber formation is achieved with similar success. In the case of a nitrite ester solution where a N,N-dialkylacylamide is used as the proton acceptor, it may be advantageous to neutralize or slightly alkalize the solution to eliminate the reactivity to moisture and add the catalyst to the protic solvent. The protic solvent to be used depends largely on the polyhydroxypolymer to be regenerated. For most polysaccharides and synthetic polyhydroxypolymers, anhydrous or aqueous alcohols, such as methanol, ethanol, isopropanol, and the like, are required because of the water solubility of these polymers. In the case of cellulose or a mixture of a substantial amount of cellulose and another polyhydroxypolymer, water may be used as well. At times, it is advantageous, i.e., the polymer separation is improved, if the protic solvent is mixed with another type of solvent provided that this second solvent does not inactivate the catalyst and that it is completely miscible with the protic solvent as well as with the nitrite ester solvent.

In addition to the polyhydroxypolymer nitrite esters, other soluble polymers may be added to the nitrite ester solution. This may be done by dissolving the polymer directly in the reaction mixture containing the nitrite ester or by pre-dissolving the polymer in a suitable solvent and adding the resulting solution to the nitrite ester solution or vice versa. Although, because of simplified solvent recovery, it is preferred to use the same solvent as contained in the nitrite ester reaction mixture, other aprotic solvents, such as chlorinated hydrocarbons, hydrocarbons, alkylesters, aromatics, acetonitrile, dioxane, and the like, may be used for pre-dissolving the polymer provided that such solvent is compatible, i.e., completely miscible, with the nitrite ester reaction solution and with the protic solvent to be contacted with subsequently. Of course, if the nitrite ester solution is neutral or alkaline, i.e., does not contain the acidic catalyst, such solvent may also be protic as typified by alcohol and water. In this case, the acidic catalyst is added to the protic solvent to be used subsequently for the regeneration of the polyhydroxypolymer and the separation of the polymer mixture in the form of certain shaped articles. The type of additional polymer which may be added to the nitrite ester solution may be any polymeric compound which either does not contain any hydroxyl groups or the hydroxyl groups of which are essentially completely substituted. Polymers of that type are synthetic polymers typified by polyacrylic esters, methacrylic esters, polyacrylonitrile, and other acrylics, polyvinylesters, -ethers, and -halides, vinyl and acrylic copolymers, polystyrene and copolymers, ethylene copolymers, propylene copolymers, phenolics, polyamides such as nylon, polyethers, polyesters, polyalkyleneglycols, and others and highly substituted polysaccharides typified by their nitrate, acetate, propionate, and other esters, their methyl, ethyl, and other ethers, and the like. The only requirements are that such polymer is soluble in one or more of the above solvents, that it is compatible with the polymeric nitrite ester solution, and that it can be separated simultaneously with the polyhydroxypolymer by the proper choice of the protic solvent or the solvent mixture containing the protic solvent. A limited amount of an additive, such as a plasticiser, or of a liquid lower molecular weight polymer may be added also provided, of course, that it is retained in the film or fiber and not leached out during film or fiber formation. Films, fibers, and other shaped objects are obtained by contact with a protic solvent in the presence of an acidic catalyst in the way described above. As already mentioned, the choice of the protic solvent depends on the polymer mixture, and it should be selected in such a way that, on contact, regeneration of the polyhydroxypolymer and separation of both the polyhydroxypolymer and the polymer lacking hydroxyl groups occur essentially simultaneously. Of course, prior to contact with a protic solvent, part or most of the polymer solvent, especially in the case of a low boiling solvent, may be evaporated and, thus, the polymer concentration increased. This often improves fiber and film formation.

The shaped articles obtainable by my process consist of homogeneous and intimate mixtures of the polymers originally present in the polymeric nitrite ester solution. Thus, they may consist of only one polyhydroxypolymer, or they may consist of a combination of several polyhydroxypolymers or of one or more polyhydroxypolymers and one or more polymers lacking hydroxyl groups. Of course, if desired, unreacted cellulose fibers may be included in such articles by suspending the desired amount of cellulose fiber in the polymer solution prior to film or fiber formation. In combination of several polymers, the polymer ratio can be chosen arbitrarily, and the weight percentage of any polymer may vary between about 0.1 and 99.9.

Shaped articles containing acidic polymers, such as polymeric sulfuric or phosphoric acid esters, polyuronic acids, polyacrylic acid, and the like, may be modified further by neutralizing with various bases, such as alkali, ammonium, and alkali earth hydroxides and the various primary, secondary, and tertiary amines. Also, the alkali salt of such acidic compound may be treated with a quaternary ammonium halide resulting in an exchange of the alkali ion by the quaternary ammonium ion. This will produce property changes of the shaped object, such as increased or reduced water sensitivity or even water repulsion depending on the ion selected.

The usefulness of the shaped articles, particularly films and fibers, is obvious and need not be demonstrated. Films of cellulose, cellulose acetate, and cellulose nitrate, for example, are used in packaging material, membranes, and the like, films or other polysaccharides are used as food packaging materials, and fibers of cellulose, polyesters, polyamides, and other polymers are used in the manufacture of, for example, textiles. The novel combination of several polymers as described in this invention, such as cellulose-polyester, cellulose-polyvinylalcohol, polyvinylalcohol-nylon, and the like, in the same film or fiber will combine some of the advantages of the individual polymers but also will add new properties, such as possibly higher strength, increased flexibility, improved dyability, antistatic properties, and the like. The incorporation of a negatively charged polymer in, for example, cellulose or cellulose acetate films may be useful in their application as osmotic membranes or, because of the added protein reactivity, in the meat industry as, for example, sausage casing and in medical applications.

The following examples illustrate specific preferred embodiments of this invention and are not intended to be limiting.

EXAMPLE XVIII

High molecular weight cotton linter pulp (10 g.) was suspended in 300 ml. DMF and, under exclusion of moisture, 16 g. dinitrogentetroxide was introduced slowly and with mechanical agitation. Strong agitation was continued until a clear highly viscous solution was obtained. Part of the solution was spread evenly on a glass plate in a low humidity chamber and then sprayed with anhydrous or aqueous methanol, the film removed, blotted between filter paper, immersed in and washed with methanol, and dried. The film was clear and strong. Fibers of high clarity and strength were obtained by extruding the solution through fine nozzles into methanol, washing the resulting fibers with fresh methanol, and drying. If droplets of the solution were dropped into methanol, washed with methanol, and dried, the product was obtained in the form of granules. The granular size depended on the concentration of the cellulose in the solution and on the size of the droplets.

Similar results were obtained when a lower molecular weight cellulose or cellulose from other sources was used or when the cellulose was replaced by polyvinyl alcohol, starch, hemicellulose, guar gum, locust bean gum, alginic acid, pectic acid, hydroxyethyl cellulose, methyl cellulose with a D.S. of about 1.5, or propylene glycol alginate.

EXAMPLE XIX

Cotton linter pulp (5 g.) and 5 g. polyvinyl alcohol were suspended in 200 ml. DMF, and sufficient dinitrogentetroxide was introduced to result in a clear viscous solution on prolonged mixing. Films, fibers, and granules were obtained from this solution as described under Example XVIII. Substitution of nitrosyl chloride for dinitrogentetroxide or of a mixture of DMF and benzene for DMF produced similar results.

The same results were obtained when the ratio of the two polymers was changed to 8:2 or 2:8 and/or when other polymer mixtures were used, such as cellulose-starch, cellulose-cellulose sulfuric acid ester, cellulose-carrageenan, cellulose-alginic acid, cellulose-pectic acid, cellulose-guar gum, cellulose-gum arabic, starch-alginic acid, starch-pectic acid, and when mixtures of three or more of the above polymers were used.

If the methanol used for separating films and fibers was replaced by ethanol, isopropanol, aqueous acetone, and methanol-acetone mixtures, films, fibers, and granules of the polymers were obtained equally well.

Films, fibers, and granules containing an acidic polyhydroxypolymer were neutralized by immersing in aqueous or anhydrous methanol containing ammonium, sodium, or potassium hydroxides, propylamine, dibutylamine, trilaurylamine, or triethanolamine. Softness, flexibility, water sensitivity, and other characteristics of the products depended to some extent on the base used for neutralization.

EXAMPLE XX

Cellulose (10 g.) was suspended in 200 ml. DMF and about 15 g. dinitrogentetroxide introduced to obtain a clear solution. A solution of 10 g. of polyvinyl acetate in 50 ml. ethylacetate was added, and from this mixture, films and fibers were prepared in a manner described under Example XVIII. Films and fibers were obtainable equally well when starch, alginic acid, guar gum, or hydroxypropyl cellulose was substituted for cellulose and/or cellulose nitrate, cellulose acetate, polyacrylic ester, or polymethacrylic ester substituted for polyvinyl acetate.

In another experiment, the polyvinyl acetate solution was replaced by a solution of 10 g. of nylon in hot DMF and, in a further experiment, by 10 g. polyethylene glycol in DMF, and films and fibers were prepared with equal success.

Changing the ratios of the polymers in the solutions did not adversely affect film and fiber formation.

EXAMPLE XXI

Polyvinyl alcohol (10 g.) was suspended in 80 ml. DMAC, about 10 g. dinitrogentetroxide introduced with mechanical stirring and under exclusion of moisture, and stirring continued until a clear solution was obtained. Then, a solution of 10 g. polyacrylonitrile in 50 ml. DMAC was added and the resulting clear solution of the polymer mixture used for film and fiber formation. A mixture of benzene-isopropanol-water was used for separation of the polymers, and isopropanol was used for washing.

Essentially similar results were obtained when the polyacrylonitrile solution was replaced by solutions of methyl vinyl ether-maleic anhydride copolymer, polyester, polyvinyl chloride, polyketone, phenolic resin, ethylene-acrylic acid copolymer, or polystyrene, or by a solution of two of such polymers and/or polyvinyl alcohol was substituted by guar gum or a mixture of cellulose and starch.

EXAMPLE XXII

Hydroxyethyl cellulose (10 g.) was solubilized in a mixture of 85 ml. DMF and 15 ml. pyridine by introducing a sufficient amount of dinitrogentetroxide and the resulting solution mixed with a solution of polyvinyl hydrogenphthalate (10 g.) in DMAC. The resulting solution of the two polymers then was spread on glass plates and the plates immersed in aqueous ethanol containing hydrochloric acid in excess to the amount of pyridine on a molar basis. The films then were removed, washed with ethanol, kept in ethanol containing a small amount of ammonia, and dried.

EXAMPLE XXIII

Cellulose (10 g.) was solubilized in a mixture of 50 ml. DMF and 50 ml. ethyl acetate with a sufficient amount of dinitrogentetroxide, and a solution of 12 g. cellulose acetate in 100 ml. ethyl acetate was added. The resulting solution was spread on glass plates in a low humidity chamber, most of the solvent removed by evaporation under reduced pressure, and the plates immersed in methanol. The films were washed with methanol and dried.

Similar results were obtained when polyvinyl acetate was substituted for cellulose acetate and/or alginic acid for cellulose.

I claim:

1. A process of preparing films, fibers or other shaped articles comprising cellulose, which process comprises forming a cellulose nitrite ester by reacting dinitrogen tetroxide or nitrosyl chloride with activated cellulose that contains about 4 to 12 percent by weight of water which is homogeneously distributed within the cellulose, said reaction being conducted in a reaction medium containing a solubilizing agent for the cellulose nitrite ester and a proton acceptor which is a highly polar aprotic solvent or a weak tertiary amine base at a temperature of below about 50° C., bringing the reaction mixture containing the nitrite ester into the desired shape while maintaining the temperature below about 50° C., and regenerating and separating said cellulose polymer from said reaction mixture by contact with a protic solvent in the presence of an acid catalyst to form films, fibers or other shaped articles of essentially unmodified cellulose.

2. A process of preparing films, fibers or other shaped articles comprising cellulose, which process comprises forming a cellulose nitrite ester by reacting dinitrogen tetroxide or nitrosyl chloride with activated cellulose in which cellulose containing in excess of about 4 percent by weight of water uniformly distributed within the cellulose is treated with a highly polar aprotic solvent or a weak tertiary amine base to reduce the water content of the cellulose to below about 4 percent, said reaction being conducted at a temperature below about 50° C. in a reaction medium containing a solubilizing agent for the resulting cellulose nitrite ester and a proton acceptor which is a highly polar aprotic solvent or a weak tertiary amine base, bringing the reaction mixture containing the nitrite ester into the desired shape while maintaining the temperature below about 50° C., and regenerating and separating said cellulose polymer from said reaction mixture by contact with a protic solvent in the presence of an acid catalyst to form films, fibers or other shaped articles of essentially unmodified cellulose.

3. A process of preparing films, fibers or other shaped articles comprising a homogeneous and intimate mixture of starch or a starch fraction and an organic-solvent-soluble polymer substantially lacking hydroxyl groups which comprises reacting gelatinized starch or a starch fraction with dinitrogen tetroxide or nitrosyl chloride in a reaction medium containing a solubilizing agent for the resulting starch nitrite or nitrite ester of the starch fraction and a proton acceptor which is a highly polar aprotic solvent or a weak tertiary amine base at a temperature of below about 50° C., forming a solution containing both said starch nitrite or nitrite ester of the starch fraction and said organic-solvent-soluble polymer substantially lacking hydroxyl groups, bringing said solution to the desired shape while maintaining the temperature below about 50° C. and contacting said solution in the presence of an acid catalyst in a sufficient amount to regenerate the starch or starch fraction and to effect its separation from the medium at a given rate while separating the organic-solvent-soluble polymer substantially lacking hydroxyl groups from the medium at substantially the same rate, to form films, fibers or other shaped articles which are composed of a homogeneous and intimate mixture of essentially unmodified starch or starch fraction and said organic-solvent-soluble polymer substantially lacking hydroxyl groups.

4. The process of claim 3 wherein said solution contains also a nitrite ester of a polyhydroxy polymer other than starch or a starch fraction and said films, fibers or other shaped articles are composed of a homogeneous and intimate mixture of essentially unmodified starch fraction, essentially unmodified polyhydroxy polymer other than starch or a starch fraction and said organic-solvent-soluble polymer substantially lacking hydroxyl groups.

5. The process of claim 4 wherein said polyhydroxy polymer other than starch or a starch fraction is cellulose.

6. The process of claim 5 wherein said organic-solvent-soluble polymer substantially lacking hydroxyl groups is absent and said films, fibers or other shaped articles are composed of a homogeneous and intimate mixture of essentially unmodified starch or starch fraction and essentially unmodified cellulose.

7. A process of preparing films, fibers or other shaped articles comprising a homogeneous and intimate mixture of polyvinyl alcohol and an organic-solvent-soluble polymer substantially lacking hydroxyl groups which comprises reacting polyvinyl alcohol with dinitrogen tetroxide or nitrosyl chloride in a reaction medium containing a solubilizing agent for the resulting nitrite ester of polyvinyl alcohol and a proton acceptor which is a highly polar aprotic solvent or a weak tertiary amine base at a temperature below about 50° C., forming a solution containing both said nitrite ester of polyvinyl alcohol and said organic-solvent-soluble polymer substantially lacking hydroxyl groups, bringing said solution to the desired shape while maintaining the temperature below about 50° C. and contacting said solution with a protic solvent in the presence of an acid catalyst in a sufficient amount to regenerate the polyvinyl alcohol and to effect its separation from the medium at a given rate while separating the organic-solvent soluble polymer substantially lacking hydroxyl groups from the medium at substantially the same rate, to form films, fibers or other shaped articles which are composed of a homogeneous and intimate mixture of essentially unmodified polyvinyl alcohol and said organic-solvent-soluble polymer substantially lacking hydroxyl groups.

8. The process of claim 7 wherein said solution contains also a nitrite ester of a polyhydroxy polymer other than polyvinyl alcohol and said films, fibers or other shaped articles are composed of a homogeneous and intimate mixture of essentially unmodified polyvinyl alcohol, essentially unmodified polyhydroxy polymer other than polyvinyl alcohol and said organic-solvent-soluble polymer substantially lacking hydroxyl groups.

9. The process of claim 8 wherein said polyhydroxy polymer other than polyvinyl alcohol is cellulose.

10. The process of claim 9 wherein said organic-solvent-soluble polymer substantially lacking hydroxyl groups is absent and said films, fibers or other shaped articles are composed of a homogeneous and intimate mixture of essentially unmodified polyvinyl alcohol and essentially unmodified cellulose.

11. A process of preparing films, fibers or other shaped articles comprising a homogeneous and intimate mixture of polyuronate or polyuronic acid and an organic-solvent-soluble polymer substantially lacking hydroxyl groups which comprises reacting polyuronate or polyuronic acid which is substantially completely in its free acid form with dinitrogen tetroxide or nitrosyl chloride in a reaction medium containing a solubilizing agent for the resulting nitrite ester of polyuronate or polyuronic acid and a proton acceptor which is a highly polar aprotic solvent or a weak tertiary amine base at a temperature below about 50° C., forming a solution containing both said nitrite ester of the polyuronate or polyuronic acid and said organic-solvent-soluble polymer substantially lacking hydroxyl groups, bringing said solution to the desired shape while maintaining the temperature below about 50° C. and contacting said solution with a protic solvent in the presence of an acid catalyst in a sufficient amount to regenerate the polyuronate or polyuronic acid and to effect its separation from the medium at a given rate while separating the organic-solvent-soluble polymer substantially lacking hydroxyl groups from the medium at substantially the same rate, to form films, fibers or other shaped articles which are composed of a homogeneous and intimate mixture of essentially unmodified polyuronate or polyuronic acid and said organic-solvent-soluble polymer substantially lacking hydroxyl groups.

12. The process of claim 11 wherein said solution contains also a nitrite ester of a polyhydroxy polymer other than polyuronate or polyuronic acid and said films, fibers and other shaped articles are composed of a homogeneous and intimate mixture of essentially unmodified polyuronate or polyuronic acid, essentially unmodified polyhydroxy polymer other than polyuronate or polyuronic acid and said organic-solvent-soluble polymer substantially lacking hydroxyl groups.

13. The process of claim 12 wherein said polyhydroxy polymer other than polyuronate or polyuronic acid is cellulose.

14. The process of claim 13 wherein said organic-solvent-soluble polymer substantially lacking hydroxyl groups is absent and said films, fibers and other shaped articles are composed of a homogeneous and intimate mixture of essentially unmodified polyuronate or polyuronic acid and essentially unmodified cellulose.

15. The process of claim 1 or 2 wherein said reaction medium containing cellulose nitrite ester contains also a nitrite ester of a polyhydroxy polymer other than cellulose and both said cellulose nitrite ester and said nitrite ester of the polyhydroxy polymer other than cellulose are regenerated and separated by contact with a protic solvent in the presence of an acid catalyst to form films, fibers or other shaped articles of essentially unmodified cellulose and said polyhydroxy polymer in an essentially unmodified form in which the cellulose and said polyhydroxy polymer are present as a homogeneous and intimate polymer mixture.

16. The process of claim 1 or 2 wherein said reaction medium containing cellulose nitrite ester contains also an organic solvent soluble polymer substantially lacking hydroxyl groups, and the solution containing both said cellulose nitrite ester and said organic solvent soluble polymer is brought to the desired shape while maintaining the temperature below about 50° C. and then contacted with a protic solvent in the presence of an acid catalyst in a sufficient amount to regenerate the cellulose and effect its separation from the medium at a given rate while separating the organic solvent soluble polymer substantially lacking hydroxyl groups from the medium at substantially the same rate to form films, fibers or other shaped articles which are composed of a homgeneous and intimate mixture of essentially unmodified cellulose and organic solvent soluble polymer substantially lacking hydroxyl groups.

17. The process of claim 15 wherein said reaction medium containing cellulose nitrite ester and said polyhydroxy polymer nitrite ester forms a solution with an organic solvent soluble polymer substantially lacking hydroxyl groups, and the solution containing said cellulose nitrite ester, said polyhydroxy polymer nitrite ester, and said organic solvent soluble polymer is brought to the desired shape while maintaining the temperature below about 50° C. and then contacted with a protic solvent in the presence of an acid catalyst in a sufficient amount to regenerate the cellulose and the polyhydroxy polymer and effect their separation from the medium at a given rate while separating the organic solvent soluble polymer substantially lacking hydroxyl groups from the medium at substantially the same rate to form films, fibers or other shaped articles which are composed of a homogeneous and intimate mixture of essentially unmodified cellulose, essentially unmodified polyhydroxy polymer and organic solvent soluble polymer substantially lacking hydroxyl groups.

18. The process of claim 1 wherein one solvent functions as both the solubilizing agent and the proton acceptor and said one solvent is dialkylacylamide or a weak tertiary amine base which is pyridine, quinoline or isoquinoline, or mixtures thereof.

19. The process of claim 2 wherein one solvent functions as both the solubilizing agent and the proton acceptor and said one solvent is dialkylacylamide or a weak tertiary amine base which is pyridine, quinoline, or isoquinoline or mixtures thereof.

20. The process of claim 3 wherein one solvent functions as both the solubilizing agent and the proton acceptor and said one solvent is dialkylamide or a weak tertary amine base which is pyridine, quinoline or isoquinoline or mixtures thereof.

21. The process of claim 7 wherein one solvent functions as both the solubilizing agent and the proton acceptor and said one solvent is dialkylacylamide or a weak tertiary amine base which is pyridine, quinoline or isoquinoline or mixtures thereof.

22. The process of claim 11 wherein one solvent functions as both the solubilizing agent and the proton acceptor and said one solvent is dialkylacylamide or a weak tertiary amine base which is pyridine, quinoline or isoquinoline or mixtures thereof.

23. The process of claim 1 wherein the protic solvent used for regeneration is water or alcohol.

24. The process of claim 2 wherein the protic solvent used for regeneration is water or alcohol.

25. The process of claim 3 wherein the protic solvent used for regeneration is water or alcohol.

26. The process of claim 7 wherein the protic solvent used for regeneration is water or alcohol.

27. The process of claim 11 wherein the protic solvent used for regeneration is water or alcohol.

28. The process of claim 1 wherein the temperature prior to said regeneration is below about 30° C.

29. The process of claim 2 wherein the temperature prior to said regeneration is below about 30° C.

30. The process of claim 3 wherein the temperature prior to said regeneration is below about 30° C.

31. The process of claim 7 wherein the temperature prior to said regeneration is below about 30° C.

32. The process of claim 11 wherein the temperature prior to said regeneration is below about 30° C.

33. The process of claim 1 wherein the medium containing the nitrite of the polyhydroxy polymer is neutral to alkaline and the acid catalyst is present in the mixture containing the protic solvent.

34. The process of claim 2 wherein the medium containing the nitrite of the polyhydroxy polymer is neutral to alkaline and the acid catalyst is present in the mixture containing the protic solvent.

35. The process of claim 3 wherein the medium containing the nitrite of the polyhydroxy polymer is neutral to alkaline and the acid catalyst is present in the mixture containing the protic solvent.

36. The process of claim 7 wherein the medium containing the nitrite of the polyhydroxy polymer is neutral to alkaline and the acid catalyst is present in the mixture containing the protic solvent.

37. The process of claim 11 wherein the medium containing the nitrite of the polyhydroxy polymer is neutral to alkaline and the acid catalyst is presnet in the mixture containing the protic solvent.

38. The process of claim 1 wherein part of the solvent is evaporated prior to regeneration and separation of the polymer so as to increase the polymer concentration.

39. The process of claim 2 wherein part of the solvent is evaporated prior to regeneration and separation of the polymer so as to increase the polymer concentration.

40. The process of claim 3 wherein part of the solvent is evaporated prior to regeneration and separation of the polymer so as to increase the polymer concentration.

41. The process of claim 7 wherein part of the solvent is evaporated prior to regeneration and separation of the polymer so as to increase the polymer concentration.

42. The process of claim 11 wherein part of the solvent is evaporated prior to regeneration and separation of the polymer so as to increase the polymer concentration.

43. A solution of the nitrite ester of starch or a starch fraction and an organic-solvent-soluble polymer substantially lacking hydroxyl groups in an anhydrous medium containing a highly polar aprotic solvent or a weak tertiary amine base or both.

44. The solution of claim 43 which also contains a nitrite ester of polyhydroxy polymer other than starch or a starch fraction.

45. The solution of claim 44 wherein the polyhydroxy polymer other than starch or a starch fraction is cellulose.

46. The solution of claim 45 wherein said organic-solvent-soluble polymer substantially lacking hydroxyl groups is absent and said solution contains only the nitrite esters of starch or a starch fraction and of cellulose.

47. A solution of the nitrite ester of polyvinyl alcohol and an organic-solvent-soluble polymer substantially lacking hydroxyl groups in an anhydrous medium containing a highly polar aprotic solvent or a weak tertiary amine base or both.

48. The solution of claim 47 which contains also a nitrite ester of polyhydroxy polymer other than polyvinyl alcohol.

49. The solution of claim 48 wherein the polyhydroxy polymer other than polyvinyl alcohol is cellulose.

50. The solution of claim 49 wherein the organic-solvent-soluble polymer substantially lacking hydroxyl groups is absent and said solution contains only the nitrite esters of polyvinyl alchol and cellulose.

51. A solution of a nitrite ester of polyuronate or polyuronic acid and an organic-solvent-soluble polymer substantially lacking hydroxyl groups in an anhydrous medium containing a highly polar aprotic solvent or a weak tertiary amine base or both.

52. The solution of claim 51 which contains also a nitrite ester of polyhydroxy polymer other than polyuronate or polyuronic acid.

53. The solution of claim 52 wherein the polyhydroxy polymer other than polyuronate or polyuronic acid is cellulose.

54. The solution of claim 53 wherein said oganic-solvent-soluble polymer substantially lacking hydroxyl groups is absent and said solution contains only the nitrite esters of polyuronate or polyuronic acid and of cellulose.

* * * * *